United States Patent
Pugh et al.

(10) Patent No.: US 10,314,530 B2
(45) Date of Patent: Jun. 11, 2019

(54) ELECTRONIC OPHTHALMIC LENS WITH SLEEP MONITORING

(71) Applicant: Johnson & Johnson Vision Care, Inc., Jacksonville, FL (US)

(72) Inventors: Randall B. Pugh, St. Johns, FL (US); Frederick A. Flitsch, New Windsor, NY (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 81 days.

(21) Appl. No.: 14/924,065

(22) Filed: Oct. 27, 2015

(65) Prior Publication Data

US 2017/0112433 A1    Apr. 27, 2017

(51) Int. Cl.
*A61B 3/14* (2006.01)
*A61B 5/00* (2006.01)
(Continued)

(52) U.S. Cl.
CPC ............ *A61B 5/4809* (2013.01); *A61B 5/002* (2013.01); *A61B 5/1103* (2013.01); *A61B 5/18* (2013.01);
(Continued)

(58) Field of Classification Search
CPC ......... A61B 3/113; A61B 3/0041; A61B 3/16; A61B 3/10; A61B 5/002; A61B 5/1103; A61B 5/18; A61B 5/4812; A61B 5/4818; A61B 5/6815; A61B 5/6821; A61B 7/003; A61B 5/0026; A61B 5/0059; A61B 5/01; A61B 5/0496; A61B 5/0488; A61B 5/0476; A61B 5/11; A61B 5/74; A61B 5/165; A61B 5/1468; A61B 5/4076; A61B 5/4836; A61B 5/4857; A61B 5/6803; A61B 5/6814; A61B 5/7475; A61B 5/14532;
(Continued)

(56) References Cited

U.S. PATENT DOCUMENTS

2003/0021601 A1* 1/2003 Goldstein .............. G03B 17/00 396/263
2003/0139687 A1* 7/2003 Abreu .................. A61B 3/1241 600/558

(Continued)

FOREIGN PATENT DOCUMENTS

EP    2772791 A1    9/2014
EP    2846183 A2    3/2015

OTHER PUBLICATIONS

European Search Report for corresponding EPA No. 16195807.9 dated Jun. 21, 2017.

*Primary Examiner* — Mustak Choudhury

(57) ABSTRACT

An eyelid position sensor system and/or an eye movement sensor system for an ophthalmic lens having an electronic system is described herein for recording data associated with sleep of the wearer. The eyelid position sensor system is part of an electronic system incorporated into the ophthalmic lens. The electronic system in at least one embodiment includes a system controller and a data manager. In at least one embodiment, the eyelid position sensor system is utilized to determine eyelid position and the eye movement sensor system is utilized to determine eye position for the system controller to determine if the wearer is awake, asleep, or in REM sleep.

16 Claims, 26 Drawing Sheets

(51) Int. Cl.
*A61B 5/18* (2006.01)
*G01J 1/42* (2006.01)
*G02C 7/04* (2006.01)
*G02C 11/00* (2006.01)
*A61B 5/11* (2006.01)
*A61B 3/113* (2006.01)

(52) U.S. Cl.
CPC .......... *A61B 5/4812* (2013.01); *A61B 5/6821* (2013.01); *G01J 1/42* (2013.01); *G02C 7/04* (2013.01); *G02C 11/10* (2013.01); *A61B 3/113* (2013.01); *A61B 2560/0209* (2013.01)

(58) Field of Classification Search
CPC ......... A61B 5/14546; G01J 1/42; G02C 7/04; G02C 11/10; G02C 7/049; G02C 7/081; G02C 7/083; A61M 21/00; A61M 21/02; G08B 21/06; G06F 3/013

USPC .................. 351/159.75, 205, 209, 219, 246; 264/1.38; 396/263; 600/398, 558; 340/575

See application file for complete search history.

(56) References Cited

U.S. PATENT DOCUMENTS

| | | | |
|---|---|---|---|
| 2009/0207028 A1* | 8/2009 | Kubey | A61B 3/113 340/575 |
| 2012/0209355 A1 | 8/2012 | Witt | |
| 2012/0212345 A1 | 8/2012 | Harman | |
| 2013/0144743 A1 | 6/2013 | Pugh | |
| 2014/0016097 A1* | 1/2014 | Leonardi | A61B 3/0041 351/209 |
| 2014/0240655 A1 | 8/2014 | Pugh et al. | |

* cited by examiner

ELECTRONIC OPHTHALMIC LENS WITH SLEEP MONITORING

BACKGROUND OF THE INVENTION

1. Field of the Invention

The present invention relates to a powered or electronic ophthalmic lens, and more particularly, to a powered or electronic ophthalmic lens having a sensor and associated hardware and software for detecting sleep.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the pre-corneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered ophthalmic lenses may be designed to provide enhanced vision via zoom-in and zoom-out capabilities, or just simply modifying the refractive capabilities of the lenses. Electronic and/or powered contact lenses may be designed to enhance color and resolution, to display textual information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, and provide novelty image displays. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optical grade plastic. Accordingly, there exists a need for providing a mechanically and electrically robust electronic contact lens.

As these are powered lenses, energy or more particularly current consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low-cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components that is safe, low-cost, and reliable, has a low rate of power consumption and is scalable for incorporation into an ophthalmic lens.

Powered or electronic ophthalmic lenses may have to account for certain unique physiological functions from the individual utilizing the powered or electronic ophthalmic lens. More specifically, powered lenses may have to account for blinking, including the number of blinks in a given time period, the duration of a blink, the time between blinks and any number of possible blink patterns, for example, if the individual is dosing off. Blink detection may also be utilized to provide certain functionality, for example, blinking may be utilized as a means to control one or more aspects of a powered ophthalmic lens. Additionally, external factors, such as changes in light intensity levels, and the amount of visible light that a person's eyelid blocks out, have to be accounted for when determining blinks. For example, if a room has an illumination level between fifty-four (54) and one hundred sixty-one (161) lux, a photosensor should be sensitive enough to detect light intensity changes that occur when a person blinks.

Ambient light sensors or photosensors are utilized in many systems and products, for example, on televisions to adjust brightness according to the room light, on lights to switch on at dusk, and on phones to adjust the screen brightness. However, these currently utilized sensor systems are not small enough and/or do not have low enough power consumption for incorporation into contact lenses.

It is also important to note that different types of blink detectors may be implemented with computer vision systems directed at one's eye(s), for example, a camera digitized to a computer. Software running on the computer can recognize visual patterns such as the eye open and closed. These systems may be utilized in ophthalmic clinical settings for diagnostic purposes and studies. Unlike the above described detectors and systems, these systems are intended for off-eye use and to look at rather than look away from the eye. Although these systems are not small enough to be incorporated into contact lenses, the software utilized may be similar to the software that would work in conjunction with powered contact lenses. Either system may incorporate software implementations of artificial neural networks that learn from input and adjust their output accordingly. Alternately, non-biology based software implementations incorporating statistics, other adaptive algorithms, and/or signal processing may be utilized to create smart systems.

There are a variety of jobs that require the worker to be aware and awake, for example, a truck driver, a security guard and military personnel on duty. It would be counterproductive and lead to potential issues if the worker were to fall asleep while performing their duties. Many of these jobs are such that the worker is required to have mobility while performing their duties and as such a fixed base monitoring system is not practical for providing monitoring of these workers. Furthermore, there are many jobs requiring regulated amounts of sleep in off-hours, which are manually logged by the worker instead of having automatic logging of the worker's sleep to provide better records.

Accordingly, there exists a need for a means and method for detecting certain physiological functions, such as a length of eye closure or a blink. The sensor being utilized needs to be sized and configured for use in a contact lens. In addition there exists a need to detect the position of a user's eyelids. An eyelid position sensor could be used to detect that a user is falling asleep, for example, to log a data event of the wearer falling asleep. There are existing systems for detecting lid position; however, they are limited to devices like camera imagers, image recognition, and infrared emitter/detector pairs which rely on reflection off the eye and eyelid. Existing systems to detect lid position also rely on the use of spectacles or clinical environments and are not easily contained within a contact lens.

SUMMARY OF THE INVENTION

In at least one embodiment, a method for monitoring sleep with a powered ophthalmic lens, the method includes: activating the powered ophthalmic lens; initiating an accumulator on the lens to track a passage of time; determining at a first lid sampling rate whether lid closure has occurred; when lid closure is detected, sampling at least once at least one of an accelerometer and a transducer, and determining whether a threshold is exceeded, when the threshold is exceeded retrieving a reading from the accumulator; storing the accumulator reading and a reading of the at least one of the accelerometer and the transducer; and determining whether the reading is below the threshold, when the reading is below the threshold, storing an indication of a REM end and returning to sampling lid closure. In a further embodiment, the method further includes: measuring a light level with at least one photosensor present on the lens; storing the light level and current reading from the accumulator; and determining when a change in light level occurs and storing the current reading from the accumulator with the light level reading. In a further embodiment to the prior embodiment, the method further includes comparing the accumulator to a duration threshold; when the accumulator is in excess of the duration threshold, determining if the current light level approximates the initial light level reading, when initial light level is reached, terminating method. In a further embodiment to any of the previous embodiments, sampling of the at least one of the accelerometer and the transducer occurs at a first motion sampling rate until the reading exceeds the threshold, then sampling at a second motion sampling rate. In a further embodiment to any of the previous embodiments, when lid closure is detected, then sampling lid closure at a second lid sampling rate.

In at least one embodiment, a method for monitoring sleep with a powered ophthalmic lens, the method includes: activating the powered ophthalmic lens; initiating an accumulator on the lens to track a passage of time; sampling at least once at least one of an accelerometer and a transducer; and determining whether a first threshold is exceeded, when the first threshold is exceeded retrieving a reading from the accumulator, storing the accumulator reading and a reading of the at least one of the accelerometer and the transducer, and determining whether the reading is below a second threshold, when the reading is below the second threshold, storing an indication of a REM end and returning to sampling lid closure. In a further embodiment, sampling of the at least one of the accelerometer and the transducer occurs at a first motion sampling rate until the reading exceeds the threshold, then sampling at a second motion sampling rate.

In at least one embodiment, a method for monitoring sleep with a powered ophthalmic lens, the method includes: activating the powered ophthalmic lens; initiating an accumulator on the lens to track a passage of time; sampling at least one of a lid position sensor system and an eye movement sensor system; retrieving a reading from the accumulator; storing an output of the lid position sensor system, an output of the eye movement sensor system and the accumulator reading in memory; and repeating the sampling, retrieving and storing steps at a predetermined sampling rate. In a further embodiment, the eye movement sensor system includes at one of an accelerometer and a transducer. In a further embodiment to either of the previous two embodiments, the method further includes: measuring a light level with at least one photosensor present on the lens; storing the light level and current reading from the accumulator; and determining when a change in light level occurs and storing the current reading from the accumulator with the light level reading. In a further embodiment, the method further includes: comparing the accumulator to a duration threshold; when the accumulator is in excess of the duration threshold, determining if the current light level approximates the initial light level reading, when initial light level is reached, terminating method. In a further embodiment to any of the embodiments in this paragraph, when lid closure is detected, then sampling lid closure at a second lid sampling rate.

In a further embodiment to any of the previous embodiments, the method further includes: monitoring a power supply on the lens for an available energy level; when the power supply has the available energy level below a low energy threshold, performing at least one of reducing the sampling rate for at least one of the accelerometer and the transducer, reducing the sampling rate of at least one sensor, terminating further sampling of at least one of the accelerometer and the transducer, terminating further monitoring of the power supply, storing a time stamp representing low energy based on the current value in the accumulator, removing power from at least one of the accelerometer and the transducer, sampling the lid closure at a second lid sampling rate that is slower than the first sampling rate, and powering a memory where the readings are stored.

In a further embodiment to any of previous embodiments, the method further includes: monitoring available memory for storing readings; when the available memory is below a low memory threshold, performing at least one of storing a time stamp representing low memory based on the current value in the accumulator, reducing the sampling rate for at least one of the accelerometer and the transducer, terminating further sampling of at least one of the accelerometer and the transducer, storing future readings from at least one of the accelerometer and the transducer over the earliest stored readings in the memory, and deleting the stored sensor readings associated with the lowest accumulator reading and shifting the remaining stored sensor and accumulator readings in the memory.

In a further embodiment to any of previous embodiments, storing the readings includes transmitting the readings to an external device for storage. In a further embodiment, the external device stores the readings with a time stamp based on the current time on the external device. In a further embodiment to either of the previous two embodiments, the method further includes sampling light levels with the external device and storing the light level with a time stamp in memory. In a further embodiment to any of the previous three embodiments, the method further includes receiving with the external device user input for initiation of a sleep study and a termination of the sleep study.

In at least one embodiment, a powered ophthalmic lens, the powered ophthalmic lens includes: a contact lens; an eyelid position sensor system in the contact lens, the eyelid position sensor system includes a sensor array having a plurality of measurement points vertically spaced from each other to detect eyelid position and a signal conditioner configured to sample the measurement points in the sensor array to detect eyelid position and provide an output lid signal; an eye movement sensor system in the contact lens, the eye movement sensor system includes at least one sensor to track and determine eye position and a signal conditioner cooperatively associated with the sensor and configured to track and determine eye position in spatial coordinates based on information from the sensor output and provide an output movement signal; a system controller electrically connected with said eyelid position sensor system and said eye movement sensor system, said system controller configured to sample said eyelid position sensor system and said eye movement system based on at least one predetermined sampling rate; and a memory in electrical communication with said system controller, and wherein said system controller stores data based on each sample in said memory.

In at least one embodiment, a powered ophthalmic lens includes a contact lens; an eye movement sensor system in the contact lens, the eye movement sensor system includes at least one sensor to track and determine eye position and a signal conditioner cooperatively associated with the sensor and configured to track and determine eye position in spatial coordinates based on information from the sensor output and provide an output movement signal; a system controller electrically connected with said eye movement sensor system, said system controller configured to sample the eye movement sensor system based on at least one predetermined sampling rate; and a data manager in electrical communication with said system controller and having a memory, said data manager configured to store data present in any signal outputted from said system controller to said data manager in said memory. In a further embodiment, the lens further includes an eyelid position sensor system in the contact lens, the eyelid position sensor system includes a sensor array having a plurality of measurement points vertically spaced from each other to detect eyelid position and a signal conditioner configured to sample the measurement points in the sensor array to detect eyelid position and provide an output lid signal; and wherein said system controller electrically connected with said eyelid position sensor system, said system controller configured to sample said eyelid position sensor system based on at least one predetermined eyelid sampling rate.

Further to any of the above powered ophthalmic lens embodiments, the lens further includes an accumulator; and said system controller is configured to store a corresponding reading from said accumulator for each sample data set stored. Further to any of the above powered ophthalmic lens embodiments, the lens further includes a power source electrically connected to said lid position sensor system, said eye movement sensor system, and said system controller; and a resource management system in electrical communication with at least one of said power source and said memory; said resource management system configured to determine at least one of a low energy level and memory storage threshold exceeded and in response to a positive determination, said resource management system is configured to at least one of reduce all sampling rates of the system, terminate all sampling of said eyelid position sensor system and said eye movement system, and replace earlier data with newer data when memory storage threshold is exceeded.

Further to any of the above powered ophthalmic lens embodiments, the lens further includes a communications system configured to communicate with an external device. In a further embodiment, the system controller transmits any received signal output to the external device through said communications system.

Further to any of the above powered ophthalmic lens embodiments, the eye movement system includes at least one accelerometer. In a further embodiment, the eye movement sensor system signal conditioner provides an output when a signal from said at least one accelerometer exceeds a movement threshold.

In at least one embodiment, a system includes any of the above powered ophthalmic lens embodiments and a base station capable of housing said lens, said base station includes a housing having a cavity of sufficient size for at least one lens, a clock, a communication system configured to communicate with any lens inserted in said housing includes activating said lens and downloading data stored in said memory in said lens; a memory configured to store downloaded data; and means for communicating with an external computer to transmit data received from said memory in said lens.

The electronic ophthalmic lens with lid position sensor and/or an eye movement sensor in accordance with the present invention overcomes the limitations associated with the prior art as briefly described above. These sensors may be integrated into a contact lens instead of requiring a clinical environment or spectacles as is common for existing eye-facing detection systems. The sensors are of the appropriate size and current consumption for use in a contact lens. The sensors also output the information necessary for determining whether the wearer is asleep or awake.

In accordance with one aspect, the present invention is directed to a powered ophthalmic lens. The powered ophthalmic lens includes a contact lens, an eyelid position sensor system incorporated into the contact lens, an eye position sensor system, a system controller, and a data manager. The eyelid position sensor system includes a sensor array having at least one of a plurality of individual sensors spaced vertically from each other and a continuous pressure and/or capacitance sensor to detect eyelid position. The eye position sensor system includes at least one sensor to detect eye position. The system controller is configured to sample each individual sensor in the sensor array to detect eyelid position and provide an output control signal. The data manager is configured to receive the output control signal and to log data regarding sleep of the wearer. In at least one embodiment, the contact lens includes an optic zone and a peripheral zone in which the electrical components are located. In an alternative embodiment, the eyelid position sensor system includes a strip sensor in place of the plurality of individual sensors.

In accordance with yet another aspect, the present invention is directed to a powered ophthalmic lens. The powered ophthalmic lens includes an intraocular lens, an eyelid position sensor system incorporated into the intraocular lens, an eye position sensor system, a system controller, and a data manager. The eyelid position sensor system includes a sensor array having a plurality of individual sensors spaced vertically from each other to detect eyelid position. The eye position sensor system includes at least one sensor to detect eye position. The system controller is configured to sample each individual sensor to provide an output control signal. The data manager is configured to receive the output control signal and to log data regarding sleep of the wearer.

In at least one embodiment it will be advantageous to provide a mechanism in which to track sleep by a worker.

The present invention relates to a powered or electronic ophthalmic lens which may incorporate an eyelid or lid position sensor and an eye position sensor. It is known that the eyelids protect the globe in a number of ways, including the blink reflex and the tear spreading action. The blink reflex of the eyelids prevents trauma to the globe by rapidly closing upon a perceived threat to the eye. Blinking also spreads tears over the globe's surface to keep it moist and rinse away bacteria and other foreign matter. But the movement of the eyelids may also indicate other actions or functions at play. In at least one embodiment, an eyelid position sensor may be utilized to determine whether the individual wearing the electronic ophthalmic lens is asleep.

The present invention more generally relates to a powered contact lens including an electronic system, which performs any number of functions, including actuating a variable-focus optic if included. The electronic system includes one or more batteries or other power sources, power management circuitry, one or more sensors, clock generation circuitry, control algorithms and circuitry, and lens driver circuitry.

Control of a powered ophthalmic lens may be accomplished through a manually operated external device that communicates with the lens wirelessly, such as a hand-held remote unit. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change operation state, for example, between an awake operation state and an asleep operation state. Alternatively, the sensors may include, for example, a pressure sensor, a reed switch, a salinity sensor, a biosensor, and a capacitive sensor to provide a signal indicating the lens has been inserted.

The blink detection algorithm in at least one embodiment is a component of the system controller which detects characteristics of blinks, for example, if the lid is open or closed, the duration of the blink open or closed, the inter-blink duration, and the number of blinks in a given time period. The algorithm in accordance with at least one embodiment relies on sampling light incident on the eye at a certain sample rate. Predetermined blink patterns are stored and compared to the recent history of incident light samples. When patterns match, the blink detection algorithm triggers activity in the system controller, for example, to switch to a particular operation state.

The blink detection algorithm and associated circuitry in at least one embodiment operates over a reasonably wide range of lighting conditions and is preferably able to distinguish an intentional blink sequence or closed eyelids from involuntary blinks. It is also preferred that minimal training is required to utilize intentional blinks to activate and/or control the powered ophthalmic lens. The blink detection algorithm and associated circuitry of the present invention provides a safe, low cost, and reliable means and method for detecting blinks via a powered or electronic contact lens, which also has a low rate of power consumption and is scalable for incorporation into an ophthalmic lens, for at least one of activating or controlling a powered or electronic ophthalmic lens.

The present invention is also directed to a powered or electronic ophthalmic lens that incorporates an eyelid or lid position sensor.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1A:
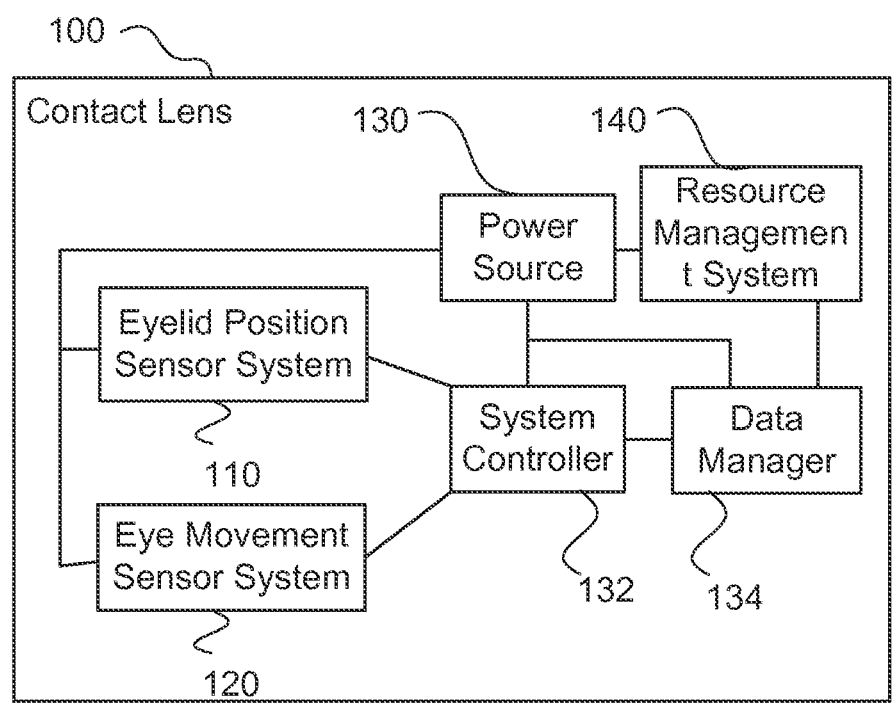
FIGS. 1A and 1B illustrate a contact lens having sensor systems in accordance with at least one embodiment of the present invention.

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, data manager, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textual information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. In addition, sensors built into the lenses may be utilized to detect light incident on the eye to compensate for ambient light conditions or for use in determining blink patterns and whether the wearer is asleep or awake.

The powered or electronic contact lens of at least one embodiment includes the necessary elements to monitor sleep of the wearer with or without elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may have a variable-focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens intended for single-use daily disposability.

The present invention may be employed in a powered ophthalmic lens or powered contact lens having an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens. Alternatively, the contact lens may just monitor sleep of the wearer including rapid eye movement (REM) sleep in at least one embodiment.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may detect blinks, blink patterns, eyelid closures, and/or eye movement. Based upon the pattern or sequence of blinks and/or movement, the powered ophthalmic lens may change operation state, for example, the operation state of the lens to begin monitoring sleep by the wearer. A further alternative is that the wearer has no control over operation of the powered ophthalmic lens.

FIG. 1A illustrates a sleep monitoring system according to at least one embodiment. The illustrated system includes an eyelid position sensor system 110, an eye movement sensor system 120, a system controller 132 and a data manager 134. The sensor systems are in electrical communication with the system controller 132, which in turn is in electrical communication with the data manager 134. In at least one embodiment, the data manager 134 includes an accumulator connected to a memory. In at least one embodiment, the data manager 134 is consolidated with the system controller 132.

Figure 1B:
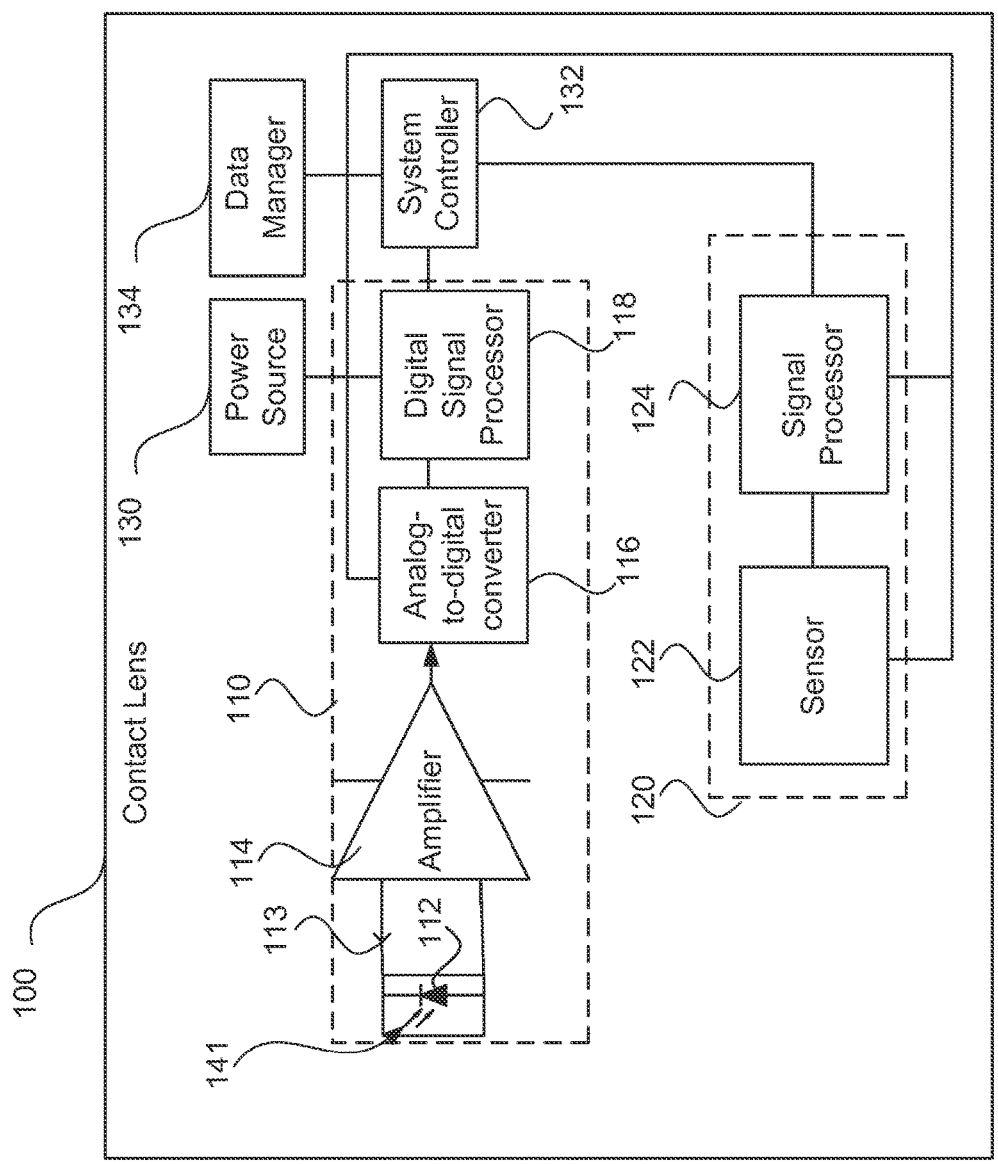

The illustrated eyelid position sensor system 110 in FIG. 1B includes at least one sensor in electrical communication with a signal processing component(s). The at least one sensor allows for the detection of eyelid closure and may take a variety of forms as is discussed later in this disclosure.

The illustrated eye movement sensor system 120 in FIG. 1B includes at least one sensor in electrical communication with a signal processor. The at least one sensor may take a variety of forms as is discussed later in this disclosure. Examples include an accelerometer and a transducer.

In an alternative embodiment, an integrated circuit or other electrical component that houses the system controller also houses the signal processing of the two sensor systems.

FIG. 1A also illustrates a power source 130 that, in at least one embodiment, provides power to the other components of the system. FIG. 1A illustrates an optional resource management system 140, which will be discussed later.

The system controller in at least one alternate embodiment uses a blink detection method which detects characteristics of blinks, for example, is the lid open or closed, the duration of the blink, the inter-blink duration, the number of blinks in a given time period, and the length of lid closure. The method in accordance with at least one embodiment relies on sampling light incident on the eye at a certain sample rate. Predetermined blink patterns are stored and compared to the recent history of incident light samples. When patterns match, the blink detection may trigger activity in the system controller, for example, to activate sleep monitoring or deactivate sleep monitoring. The blink detection in a further embodiment distinguishes between the pre-determined blink patterns and the eyelid movements associated with drowsiness or sleep onset.

Blinking is the rapid closing and opening of the eyelids and is an essential function of the eye. Blinking protects the eye from foreign objects, for example, individuals blink when objects unexpectedly appear in proximity to the eye. Blinking provides lubrication over the anterior surface of the eye by spreading tears. Blinking also serves to remove contaminants and/or irritants from the eye. Normally, blinking is done automatically, but external stimuli may contribute as in the case with irritants. However, blinking may also be purposeful, for example, for individuals who are unable to communicate verbally or with gestures can blink once for yes and twice for no. The blink detection method and system in one alternative embodiment utilizes blinking patterns that cannot be confused with normal blinking response. In other words, if blinking is to be utilized as a means for controlling an action, then the particular pattern selected for a given action cannot occur at random; otherwise inadvertent actions may occur. As blink speed and/or frequency may be affected by a number of factors, including fatigue, concentration, boredom, eye injury, medication and disease, blinking patterns for control purposes preferably account for these and any other variables that affect blinking. The average length of involuntary blinks is in the range of about one hundred (100) to four hundred (400) milliseconds. Average adult men and women blink at a rate of ten (10) involuntary blinks per minute, and the average time between involuntary blinks is about 0.3 to seventy (70) seconds. Eyelid movements may also indicate other conditions such as drowsiness as the eyelids have a general trend towards closing over a period of time or are closed for a period of time indicating that the wearer is asleep.

Blink detection may be summarized in the following steps.

1. Define an intentional "blink sequence" that a user will execute for positive blink detection or that is representative of sleep onset.

2. Sample the incoming light level at a rate consistent with detecting the blink sequence and rejecting involuntary blinks.

3. Compare the history of sampled light levels to the expected "blink sequence," as defined by a blink template of values.

4. Optionally implement a blink "mask" sequence to indicate portions of the template to be ignored during comparisons, e.g. near transitions. This may allow for a user to deviate from a desired "blink sequence," such as a plus or minus one (1) error window, wherein one or more of lens activation, control, and focus change can occur. Additionally, this may allow for variation in the user's timing of the blink sequence.

It should be appreciated that a variety of expected or intended blink patterns may be programmed into a device with one or more active at a time and in at least one embodiment control the use of particular blink patterns to be used in a particular operation state. More specifically, multiple expected or intended blink patterns may be utilized for the same purpose or functionality, or to implement different or alternate functionality. For example, one blink pattern may be utilized to cause the lens to change operation state between at least an asleep operation state and an awake operation state. The blink detection in at least one embodiment also can detect when the eyelids remain closed, which would be detected as a continuous blink; the eyelids have a movement trajectory to closing for sleep, which would be detected as a partial blink or series of partial blinks such as when a portion of the sensors are covered by an eyelid after a blink has occurred; and eyelid droop, which would be detected as a change in the steady state position of the upper and/or lower eyelid from its normal steady state position, for example, with or without confirmation of gaze position and/or head droop.

An example of a way to determine if the wearer is nodding off is by tracking the length of blink period widths and eyelids open period widths. Alternatively, also partial eyelids open period widths are tracked in addition or instead of eyelids open period widths. Typically the ratio will be 1:15 to 1:22 between blinks and eyelids open, but as the wearer approaches sleep the length of blink period widths will increase while eyelid open period widths will decrease. In a system that includes a plurality of registers for storing the period widths, a running series of ratios between blink periods and eyelid open periods may be maintained such that as that trend of ratios approaches a predetermined drowsy threshold, the wearer is probably starting to doze off. Examples of the predetermined drowsy threshold include, but are not limited to, one to 1, 2, 3, 4, 5, and 10. The system controller would be configured to compare the ratios and track the period lengths over a rolling window. In an alternative embodiment, the system controller would retain only period width information associated with non-standard blinks for a predetermined window as the wearer may notice they are dozing and be more attentive before having another lengthy blink period. In at least one embodiment, when the wearer is detected to be nodding off, the sampling frequency of the sensor(s) may increase to increase the data resolution. In a further embodiment, the data manager logs when a sampling frequency is changed and in a still further embodiment, an identification of the sampling frequency being used is stored.

In an alternative embodiment, the system controller would determine a ratio of blink to eyelids open for the wearer at a predetermined time(s). Examples of the predetermined time(s) include, but are not limited to, shortly after lens insertion, one hour increments, two hour increments, four hour increments and any combination of these. In an alternative or further embodiment, the system controller would determine a ratio of blink to eyelids open for the wearer when a change of focus of one or both eyes is detected or there is an increase in the time between blinks such that the increase exceeds a predetermined threshold indicating, for example, that the wearer is concentrating on something or boredom has set in for the wearer. This wearer-specific ratio would be used to calculate the predetermined drowsy threshold. An example of the calculation includes taking a fraction of the wearer-specific ratio, such as reducing by a quarter (e.g., 1:20 to 1:15), half (e.g., 1:20 to 1:10) or three quarters (e.g., 1:20 to 1:5). Based on this example, one of ordinary skill in the art should appreciate that a variety of reductions are possible.

A further example of nodding off is the speed at which the eyelids open and close during a blink. A study found that the mean time for eyelid closure was 92 msec plus or minus 17 msec and the mean time for eyelid opening was 242 msec plus or minus 55 msec. BanderWert et al., "Eyelid Movements: Behavioral Studies of Blinking in Humans under Different Stimulus Conditions," Journal of Physiology, May 2003, vol. 89, no. 5, pp. 2784-2796. The system controller in at least one embodiment maintains a running list of times for at least one of eyelid closure and eyelid opening to allow for a determination if there is a change in speed of the monitored eyelid movement. Such that when the speed over a series of blinks slows, then the system controller has a basis on which to determine that the wearer is drowsy. In a further embodiment, the speed is measured as a ratio between the distance from the closed eyelid position and the open eyelid position and the time to travel between these two points.

A still further example of nodding off is a decrease in the Saccades movement of the pupil of the lens wearer. It is normal when a person is awake that their eyes dart about in a Saccades movement due to physiological considerations. As a person becomes drowsy, these movements will decrease while the eyelids are open. The eye movement sensor system in at least one embodiment is used to track movement of the pupil and can provide this information to the system controller for comparison along a running list of eye movement data reflecting the volume, the length, and the speed of pupil movement.

In a further embodiment, the system controller would utilize signals from the accelerometer to determine if the wearer's head is beginning to droop in conjunction with any longer blink period width, then the system controller in at least one embodiment will lower the drowsy threshold or alternatively use the drooping head as confirmation that the wearer is beginning to doze off and requires alerting.

FIG. 1B illustrates, in block diagram form, a contact lens 100 in accordance with at least one embodiment. In the illustrated embodiment, the contact lens 100 includes an eyelid position system 110, an eye movement sensor system 120, a power source 130, a system controller 132, and a data manager 134. The illustrated eyelid position system 110 includes a photosensor 112, an amplifier 114, an analog-to-digital converter (or ADC) 116, and a digital signal processor 118. The illustrated eye movement sensor system 120 includes a sensor 122 and a signal processor 124 such as an acquisition sampling signal conditioner.

When the contact lens 100 is placed onto the front surface of a user's eye the electronic circuitry of the blink detector system may be utilized to implement the blink detection in at least one embodiment. The photosensor 112, as well as the other circuitry, is configured to detect blinks, various blink patterns produced by the user's eye, and/or level of eyelid closure.

In this embodiment, the photosensor 112 may be embedded into the contact lens 100 and receives ambient light 141, converting incident photons into electrons and thereby causing a current, indicated by arrow 113, to flow into the amplifier 114. The photosensor or photodetector 112 may include any suitable device. In one embodiment, the photosensor 112 includes a photodiode. In at least one embodiment, the photodiode is implemented in a complimentary metal-oxide semiconductor (CMOS process technology) to increase integration ability and reduce the overall size of the photosensor 112 and the other circuitry. The current 113 is proportional to the incident light level and decreases substantially when the photodetector 112 is covered by an eyelid. The amplifier 114 creates an output proportional to the input, with gain, and may function as a transimpedance amplifier which converts input current into output voltage. The amplifier 114 may amplify a signal to a usable level for the remainder of the system, such as giving the signal enough voltage and power to be acquired by the ADC 116. For example, the amplifier may be necessary to drive subsequent blocks since the output of the photosensor 112 may be quite small and may be used in low-light environments. The amplifier 114 may be implemented as a variable-gain amplifier, the gain of which may be adjusted by the system controller 132, in a feedback arrangement, to maximize the dynamic range of the system. In addition to providing gain, the amplifier 114 may include other analog signal conditioning circuitry, such as filtering and other circuitry appropriate to the photosensor 112 and amplifier 114 outputs. The amplifier 114 may include any suitable device for amplifying and conditioning the signal output by the photosensor 112. For example, the amplifier 114 may include a single operational amplifier or a more complicated circuit comprising one or more operational amplifiers. The photosensor may be a switchable array of photodiodes, and the amplifier may be an integrator. As set forth above, the photosensor 112 and the amplifier 114 are configured to detect and isolate blink sequences based upon the incident light intensity received through the eye and convert the input current into a digital signal usable ultimately by the system controller 132. In at least one embodiment, the system controller 132 is preprogrammed or preconfigured to recognize various blink sequences, blink patterns, an/or eyelid closures (partial or complete) in various light intensity level conditions and provide an appropriate output signal to the data manager 134. In at least one embodiment, the system controller 132 also includes associated memory.

In this embodiment, the ADC 116 may be used to convert a continuous, analog signal output from the amplifier 114 into a sampled, digital signal appropriate for further signal processing. For example, the ADC 116 may convert an analog signal output from the amplifier 114 into a digital signal that may be usable by subsequent or downstream circuits, such as a digital signal processor 118. The digital signal processor 118 may be utilized for digital signal processing, including one or more of filtering, processing, detecting, and otherwise manipulating/processing sampled data to permit incident light detection for downstream use. The digital signal processor 118 may be preprogrammed with the blink sequences and/or blink patterns described above along with a blink sequence indicating prolonged eyelid closure or eyelid drift. The digital signal processor 118 also in at least one embodiment includes associated memory, which in at least one embodiment stores template and masks sets to detect, for example, blink patterns for each operation state as selected by the system controller 132. The digital signal processor 118 may be implemented utilizing analog circuitry, digital circuitry, software, or a combination thereof. In the illustrated embodiment, it is implemented in digital circuitry. The ADC 116 along with the associated amplifier 114 and digital signal processor 118 are activated at a suitable rate in agreement with the sampling rate previously described, for example, every one hundred (100) ms, which is subject to adjustment in at least one embodiment.

In at least one embodiment, any suitable device that allows for detection of movement of the eye and more particularly the pupil may be utilized as the sensor 122, and more than a single sensor 122 may be utilized. The output of the sensor 122 is acquired, sampled, and conditioned by signal processor 124. The signal processor 124 may include any number of devices including an amplifier, a transimpedance amplifier, an analog-to-digital converter, a filter, a digital signal processor, and related circuitry to receive data from the sensor 122 and generate output in a suitable format for the remainder of the system. The signal processor 124 may be implemented utilizing analog circuitry, digital circuitry, software, and/or a combination thereof. In at least one embodiment, the signal processor 124 is co-designed with the sensor 122, for example, circuitry for acquisition and conditioning of an accelerometer are different than the circuitry for a muscle activity sensor or optical pupil tracker. The output of the signal processor 124 in at least one embodiment is a sampled digital stream and may include absolute or relative position, movement, detected gaze in agreement with convergence, or other data. System controller 132 receives input from the position signal processor 124 and uses this information, in conjunction with input from the eyelid position sensor system, to determine whether the wearer is asleep.

In at least one embodiment, the signal processors 118 and 124 are combined into (or fabricated as) one signal processor.

A power source 130 supplies power for numerous components in the system. The power may be supplied from a battery, energy harvester, or other suitable means as is known to one of ordinary skill in the art. Essentially, any type of power source 130 may be utilized to provide reliable power for all other components of the system. A blink sequence in at least one embodiment may be utilized to change the operation state of the system and/or the system controller. Furthermore, the system controller 132 may control other aspects of a powered contact lens depending on input from the digital signal processor 118 and/or the signal processor 124, for example, changing the focus or refractive power of an electronically controlled lens through an actuator.

In at least one embodiment, the system controller 132 will determine the operation state of the lens based on a received blink pattern, for example, to initiate or terminate sleep monitoring although in an alternative embodiment other operational states are possible simultaneously or separately. Further to this embodiment or alternatively, the operation state will determine a set of blink templates and masks to be used by the digital signal processor 118 in that operation state along with control what the data manager 134 does in response to the system controller 132 detecting the wearer has fallen asleep. In a further alternative embodiment, the lens intended for use during a work shift will operate using just a blink template indicating sleep onset and not change operational state based on any blink pattern by the wearer.

The system controller 132 uses the signal from the photosensor chain; namely, the photosensor 112, the amplifier 114, the ADC 116 and the digital signal processing system 118, to compare sampled light levels to determine eyelid closure and/or blink activation patterns.

Figure 2:
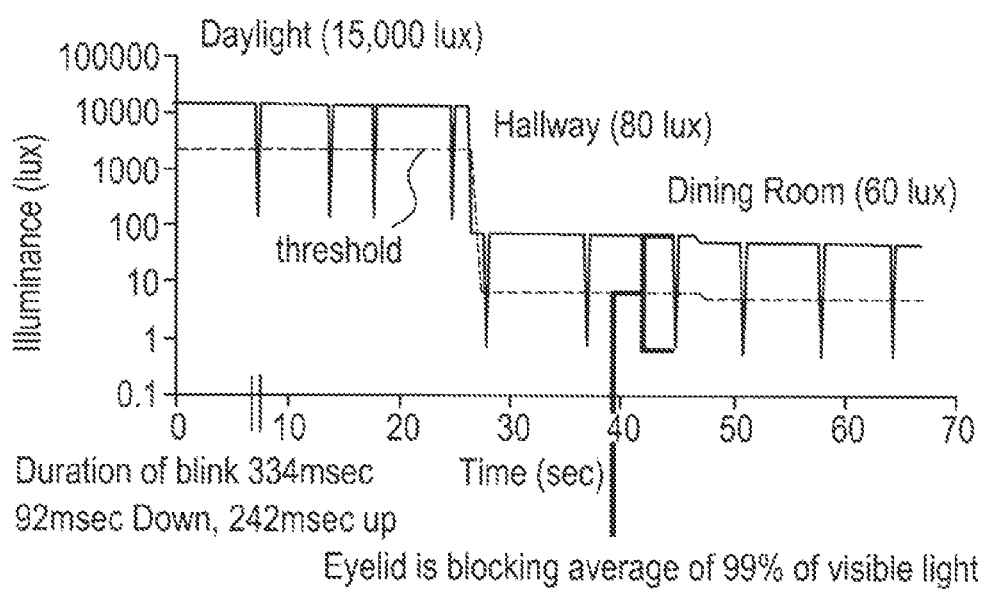
FIG. 2 illustrates a graphical representation of light incident on the surface of the eye versus time, illustrating a possible involuntary blink pattern recorded at various light intensity levels versus time and a usable threshold level based on some point between the maximum and minimum light intensity levels in accordance with at least one embodiment of the present invention.

Referring to FIG. 2, a graphical representation of blink pattern samples recorded at various light intensity levels versus time and a usable threshold level is illustrated. Accordingly, accounting for various factors may mitigate and/or prevent error in detecting blinks when sampling light incident on the eye, such as accounting for changes in light intensity levels in different places and/or while performing various activities. Additionally, when sampling light incident on the eye, accounting for the effects that changes in ambient light intensity may have on the eye and eyelid may also mitigate and/or prevent error in detecting blinks, such as how much visible light an eyelid blocks when it is closed in low-intensity light levels and in high-intensity light levels. In other words, in order to prevent erroneous blinking patterns from being utilized to control, the level of ambient light is preferably accounted for as is explained in greater detail below.

For example, in a study, it has been found that the eyelid on average blocks approximately ninety-nine (99) percent of visible light, but at lower wavelengths less light tends to be transmitted through the eyelid, blocking out approximately 99.6 percent of visible light. At longer wavelengths, toward the infrared portion of the spectrum, the eyelid may block only thirty (30) percent of the incident light. What is important to note; however, is that light at different frequencies, wavelengths and intensities may be transmitted through the eyelids with different efficiencies. For example, when looking at a bright light source, an individual may see red light with his or her eyelids closed. There may also be variations in how much visible light an eyelid blocks based upon an individual, such as an individual's skin pigmentation. As is illustrated in FIG. 2, data samples of blink patterns across various lighting levels are simulated over the course of a seventy (70) second time interval wherein the visible light intensity levels transmitted through the eye are recorded during the course of the simulation, and a usable threshold value is illustrated. The threshold is set at a value in between the peak-to-peak value of the visible light intensity recorded for the sample blink patterns over the course of the simulation at varying light intensity levels. Having the ability to preprogram blink patterns while tracking an average light level over time and adjusting a threshold may be critical to being able to detect when an individual is blinking, as opposed to when an individual is not blinking and/or there is just a change in light intensity level in a certain area.

Referring now again to FIGS. 1A and 1B, in further alternate embodiments, the system controller 132 may receive input from sources including one or more of a blink detector, pressure sensors, an accelerometer(s), photosensors, and a fob control. By way of generalization and based on this disclosure, one skilled in the art should appreciate that the method of determining sleep by the system controller 132 may use one or more inputs. For example, an electronic or powered contact lens may be programmable specific to an individual user, such as programming a lens to recognize both of an individual's blink patterns and an individual's head movements as detected with an accelerometer during the course of the day, for example, head bobbing while the eyelids are closed. In some embodiments, using more than one input to determine sleep by an electronic contact lens, such as blink detection and head movement, may give the ability for each method to be crosschecked with another before sleep onset is determined to have occurred as will be discussed later in connection with FIGS. 20 and 21. An advantage of crosschecking may include mitigation of false positives, such as minimizing the chance of unintentionally triggering a lens to alert and/or record errant data. In one embodiment, the crosschecking may involve a voting scheme, wherein a certain number of conditions are met prior to a sleep determination. In a further embodiment, the crosschecking may involve a weighted average, wherein certain inputs will be deemed more important than other inputs such as lid closure and head orientation.

In an alternate embodiment, the system controller 132 may output a signal indicating that the wearer has fallen asleep during the asleep operation state, then the data manager 134 will record the information in memory for later retrieval. In an alternative embodiment, the system controller 132 stores the data in the memory associated with the system controller 132 and does not use the data manager 134 for data storage. As discussed later, in at least one embodiment there is a clock such as an accumulator that provides a time stamp. As set forth above, the powered lens of the present invention may provide various functionalities.

Figure 17A:
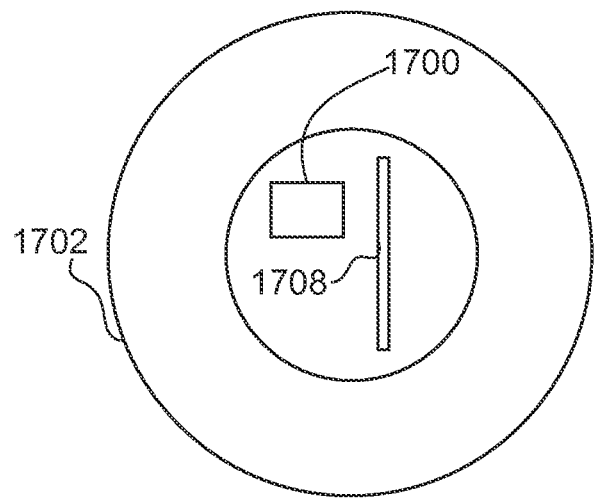
FIG. 17A-17C illustrate diagrammatic representations of an eyelid position detecting system in accordance with at least one embodiment of the present invention.
Figure 17B:
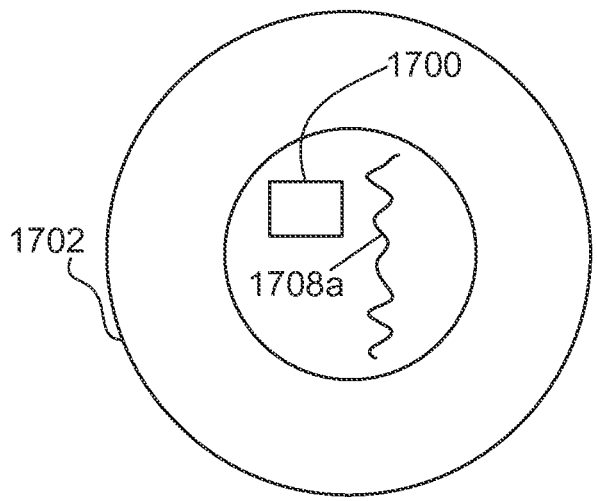
Figure 17C:
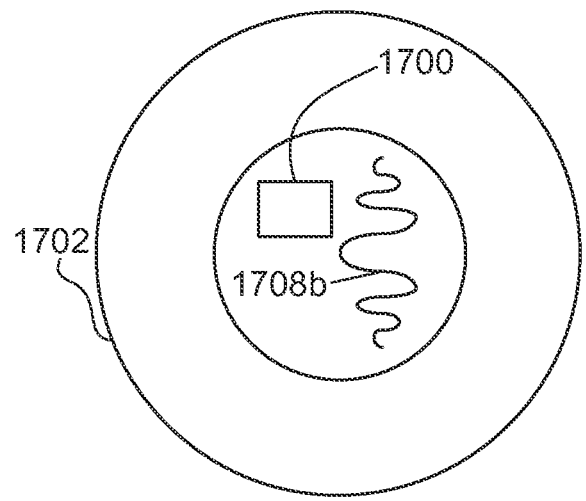
Figure 17D:
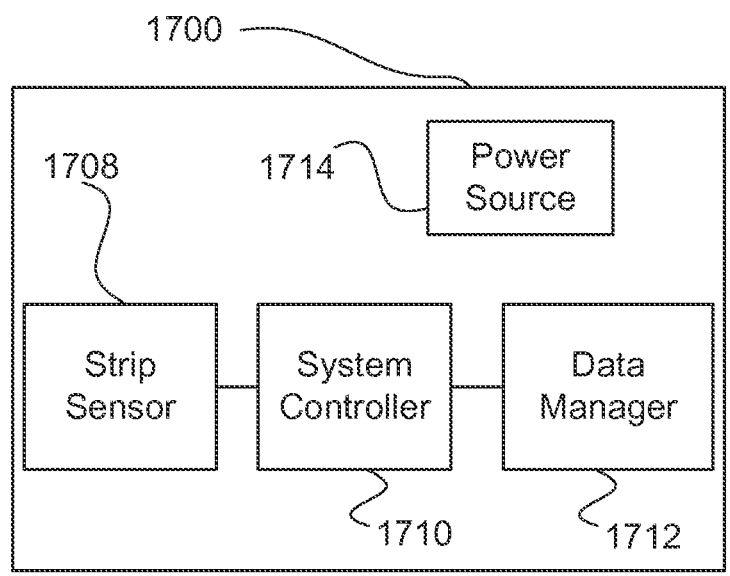
FIG. 17D illustrates an enlarged view of the electronic system of FIGS. 17A-17C.
Figures 18A, 18C:
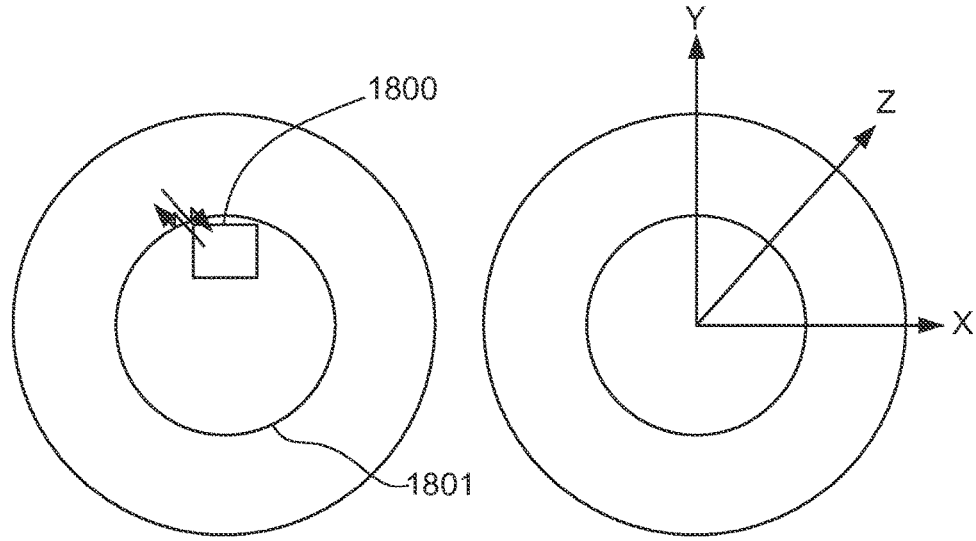
FIG. 18A illustrates a diagrammatic representation of a pupil position and convergence detection system incorporated into a contact lens in accordance with at least one embodiment of the present invention.
FIG. 18C illustrates an overlay of an X, Y, and Z axes on the eye.
Figure 18B:
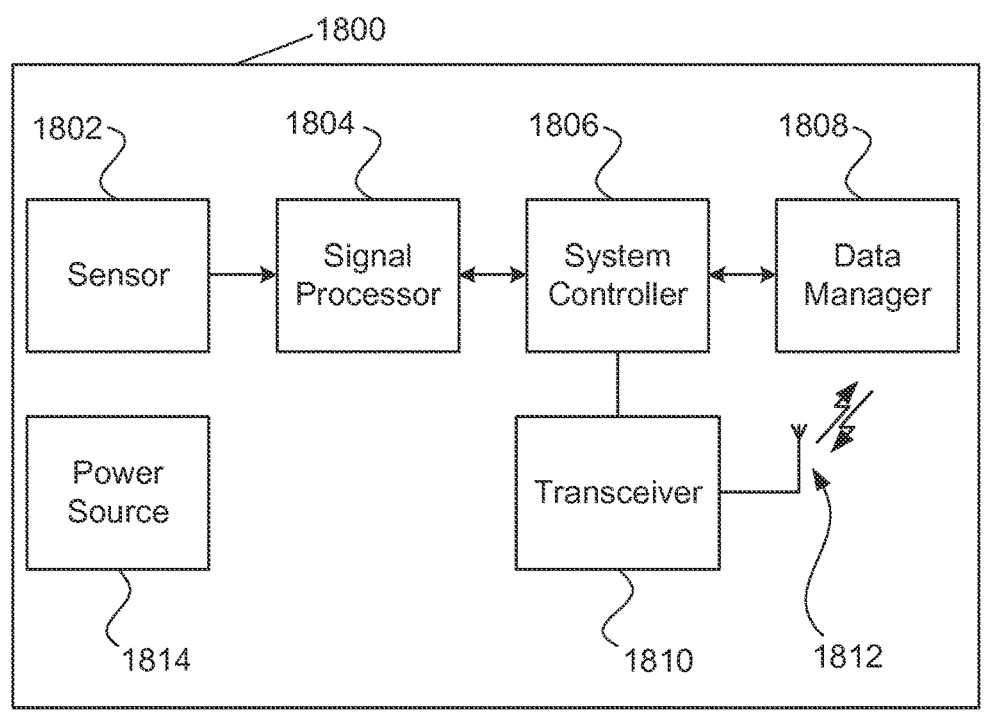
FIG. 18B is an enlarged view of the pupil position and convergence detection system of FIG. 18A.

FIGS. 3-17D provide examples of eyelid position sensor systems and FIGS. 18A-18C provide an example of an eye movement sensor system. In at least one embodiment, the eyelid position sensor systems use blink detection to determine whether the eyelid is closed and remains closed over a plurality of samples.

Figure 3:
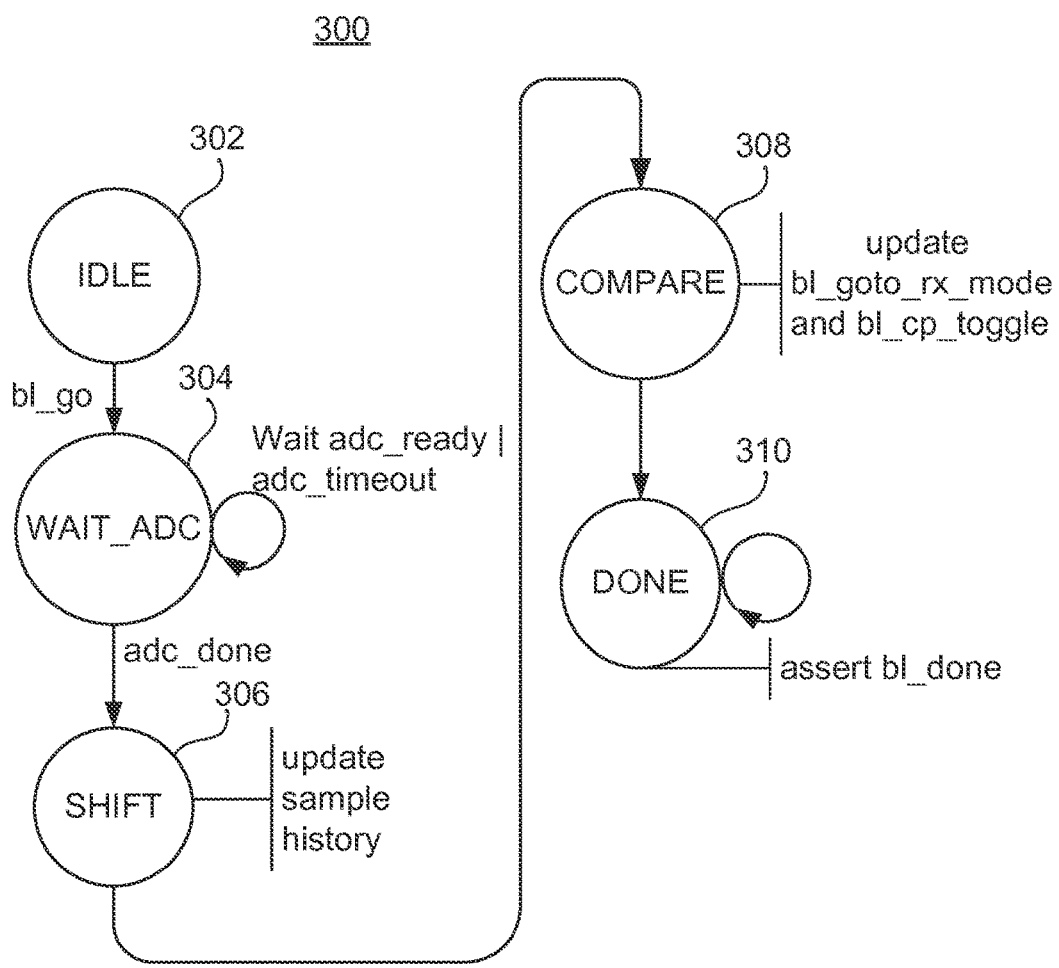
FIG. 3 is a state transition diagram of an eyelid position sensor system in accordance with at least one embodiment of the present invention.

FIG. 3 illustrates a state transition diagram 300 for an eyelid position sensor system in accordance with at least one embodiment. The system starts in an IDLE state 302 waiting for an enable signal bl_go to be asserted. When the enable bl_go signal is asserted, for example, by an oscillator and control circuit which pulses bl_go at a one hundred (100) ms rate commensurate with the blink sampling rate, the state machine then transitions to a WAIT ADC state 304 in which an ADC is enabled to convert a received light level to a digital value. The ADC asserts an adc_done signal to indicate its operations are complete, and the system or state machine transitions to a SHIFT state 306. In the SHIFT state 306 the system pushes the most recently received ADC output value onto a shift register to hold the history of blink samples. In some embodiments, the ADC output value is first compared to a threshold value to provide a single bit (1 or 0) for the sample value, in order to minimize storage requirements. The system or state machine then transitions to a COMPARE state 308 in which the values in the sample history shift register are compared to one or more blink sequence templates and masks as described above. If a match is detected, one or more output signals may be asserted, such as one to switch the state of the lens to an asleep operation state or an awake operation state or to signal onset of sleep by the wearer. The system or state machine then transitions to the DONE state 310 and asserts a bl_done signal to indicate its operations are complete.

Figure 4:
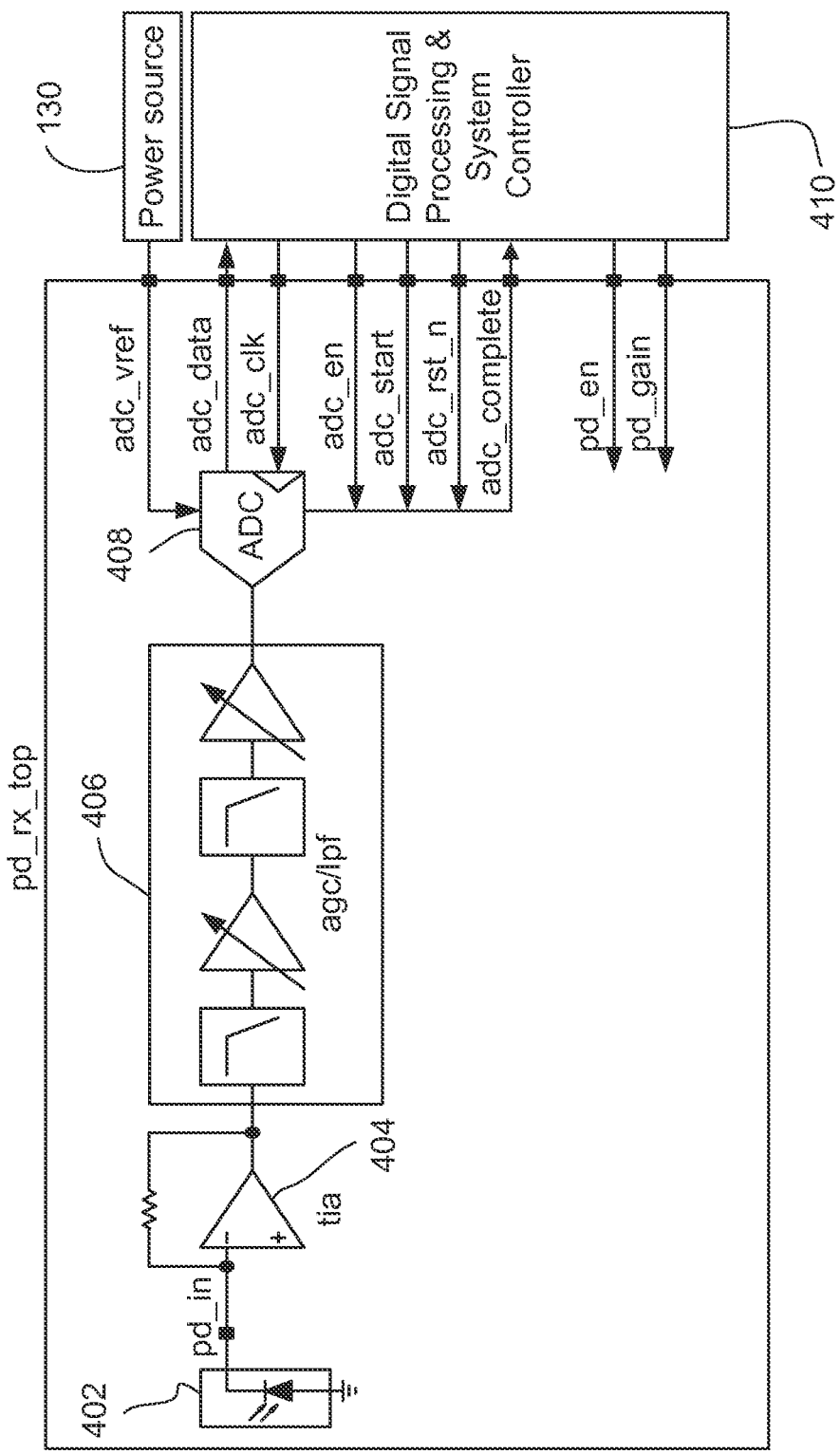
FIG. 4 illustrates a diagrammatic representation of a photodetection path utilized to detect and sample received light signals in accordance with at least one embodiment of the present invention.

FIG. 4 illustrates a photosensor or photodetector signal path pd_rx_top that may be used to detect and sample received light levels. The signal path pd_rx_top may include a photodiode 402, a transimpedance amplifier 404, an automatic gain and low pass filtering stage 406 (AGC/LPF), and an ADC 408. The adc_vref signal is input to the ADC 408 from the power source 130 (see ADC 116 in FIG. 1B) or alternately it may be provided from a dedicated circuit inside the analog-to-digital converter 408. The output from the ADC 408, adc_data, is transmitted to the digital signal processing and system controller block 118/132 (see FIG. 1B). Although illustrated in FIG. 1B as individual blocks 118 and 132, for ease of explanation, the digital signal processing and system controller are implemented on a single block 410. The enable signal, adc_en, the start signal, adc_start, and the reset signal, adc_rst_n are received from the digital signal processing and system controller 410 while the complete signal, adc_complete, is transmitted thereto. The clock signal, adc_clk, may be received from a clock source external to the signal path, pd_rx_top, or from the digital signal processing and system controller 410. It is important to note that the adc_clk signal and the system clock may be running at different frequencies. It is also important to note that any number of different ADCs may be utilized in accordance with the present invention which may have different interface and control signals but which perform a similar function of providing a sampled, digital representation of the output of the analog portion of the photosensor signal path. The photodetect enable, pd_en, and the photodetect gain, pd_gain, are received from the digital signal processing and system controller 410.

Figure 5:
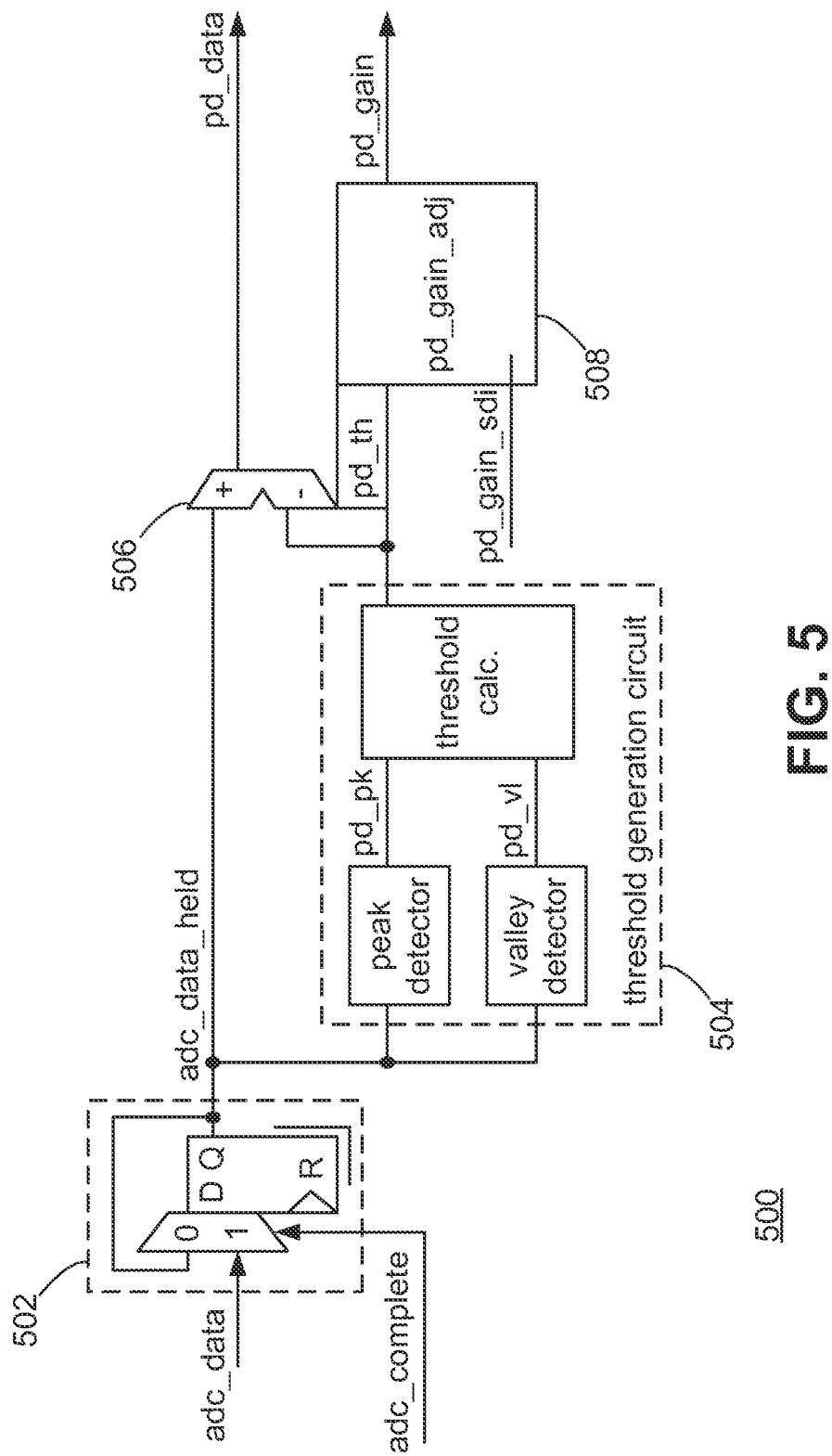
FIG. 5 illustrates a block diagram of digital conditioning logic in accordance with at least one embodiment of the present invention.

FIG. 5 illustrates a block diagram of digital conditioning logic 500 that may be used to reduce the received ADC signal value, adc_data, to a single bit value pd_data. The digital conditioning logic 500 may include a digital register 502 to receive the data, adc_data, from the photodetection signal path pd_rx_top to provide a held value on the signal adc_data_held. The digital register 502 is configured to accept a new value on the adc_data signal when the adc_complete signal is asserted and to otherwise hold the last accepted value when the adc_complete signal is received. In this manner the system may disable the photodetection signal path once the data is latched to reduce system current consumption. The held data value may then be averaged, for example, by an integrate-and-dump average or other averaging methods implemented in digital logic, in the threshold generation circuit 504 to produce one or more thresholds on the signal pd_th. The held data value may then be compared, via comparator 506, to the one or more thresholds to produce a one-bit data value on the signal pd_data. It will be appreciated that the comparison operation may employ hysteresis or comparison to one or more thresholds to minimize noise on the output signal pd_data. The digital conditioning logic may further comprise a gain adjustment block pd_gain_adj 508 to set the gain of the automatic gain and low-pass filtering stage 406 in the photodetection signal path via the signal pd_gain, illustrated in FIG. 4, according to the calculated threshold values and/or according to the held data value. It is important to note that in this embodiment six bit words provide sufficient resolution over the dynamic range for blink detection while minimizing complexity. FIG. 5 illustrates an alternative embodiment that includes providing a pd_gain_sdi control signal from, for example, the serial data interface that allows one to override the automatic gain control determined by gain adjustment block pd_gain_adj 508.

In one embodiment, the threshold generation circuit 504 includes a peak detector, a valley detector and a threshold calculation circuit. In this embodiment, the threshold and gain control values may be generated as follows. The peak detector and the valley detector are configured to receive the held value on signal adc_data_held. The peak detector is further configured to provide an output value, pd_pk, which quickly tracks increases in the adc_data_held value and slowly decays if the adc_data_held value decreases. The operation is analogous to that of a classic diode envelope detector, as is well-known in the electrical arts. The valley detector is further configured to provide an output value pd_vl which quickly tracks decreases in the adc_data_held value and slowly decays to a higher value if the adc_data_held value increases. The operation of the valley detector is also analogous to a diode envelope detector, with the discharge resistor tied to a positive power supply voltage. The threshold calculation circuit is configured to receive the pd_pl and pd_vl values and is further configured to calculate a mid-point threshold value pd_th_mid based on an average of the pd_pk and pd_vl values. The threshold generation circuit 504 provides the threshold value pd_th based on the mid-point threshold value pd_th_mid.

The threshold generation circuit 504 may be further adapted to update the values of the pd_pk and pd_vl levels in response to changes in the pd_gain value. If the pd_gain value increases by one step, then the pd_pk and pd_vl values are increased by a factor equal to the expected gain increase in the photodetection signal path. If the pd_gain value decreases by one step, then the pd_pk and pd_val values are decreased by a factor equal to the expected gain decrease in the photodetection signal path. In this manner the states of the peak detector and valley detectors, as held in the pd_pk and pd_vl values, respectively, and the threshold value pd_th as calculated from the pd_pk and pd_vl values are updated to match the changes in signal path gain, thereby avoiding discontinuities or other changes in state or value resulting only from the intentional change in the photodetection signal path gain.

In a further embodiment of the threshold generation circuit 504, the threshold calculation circuit may be further configured to calculate a threshold value pd_th_pk based on a proportion or percentage of the pd_pk value. In at least one embodiment the pd_th_pk may be advantageously configured to be seven eighths of the pd_pk value, a calculation which may be implemented with a simple right shift by three bits and a subtraction as is well-known in the relevant art. The threshold calculation circuit may select the threshold value pd_th to be the lesser of pd_th_mid and pd_th_pk. In this manner, the pd_th value will never be equal to the pd_pk value, even after long periods of constant light incident on the photodiode which may result in the pd_pk and pd_vl values being equal. It will be appreciated that the pd_th_pk value ensures detection of a blink after long intervals. The behavior of the threshold generation circuit is further illustrated in FIG. 9, as discussed subsequently.

Figure 6:
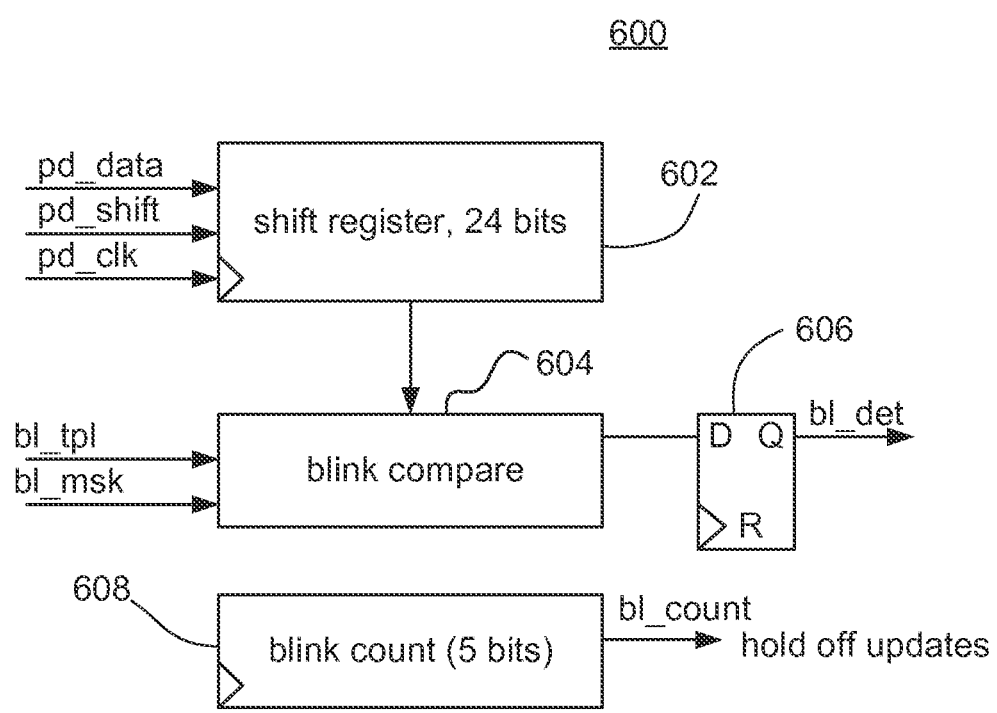
FIG. 6 illustrates a block diagram of digital detection logic in accordance with at least one embodiment of the present invention.

FIG. 6 illustrates a block diagram of digital detection logic 600 that may be used to implement digital blink detection in accordance with at least one embodiment. The digital detection logic 600 may include a shift register 602 adapted to receive the data from the photodetection signal path pd_rx_top, FIG. 4, or from the digital conditioning logic, FIG. 5, as illustrated here on the signal pd_data, which has a one bit value. The shift register 602 holds a history of the received sample values, here in a 24-bit register. The digital detection logic 600 further includes a comparison block 604, adapted to receive the sample history and one or more templates bl_tpl and masks bl_mask based on operation state (if necessary), and is configured to indicate a match to the one or more templates and masks on one or more output signals that may be held for later use. In at least one embodiment, the operation state determines the set of templates bl_tpl and masks bl_mask to be used by the comparison block 604. In at least one set of the templates bl_tpl, there is at least one sleep template representative of the wearer falling asleep. In an alternative embodiment, the digital detection logic 600 includes a comparison block, adapted to contain one or more sleep templates, and is configured to indicate a match to the one or more templates and masks on one or more output signals that may be held for later use. In such an alternative embodiment, the lens does not have asleep and awake operation states.

The output of the comparison block 604 is latched via a D flip-flop 606. The digital detection logic 600 may further include a counter 608 or other logic to suppress successive comparisons that may be on the same sample history set at small shifts due to the masking operations. In a preferred embodiment the sample history is cleared or reset after a positive match is found, thus requiring a full, new matching sequence to be sampled before being able to identify a subsequent match. The digital detection logic 600 may still further include a state machine or similar control circuitry to provide the control signals to the photodetection signal path and the ADC. In some embodiments the control signals may be generated by a control state machine that is separate from the digital detection logic 600. This control state machine may be part of the digital signal processing and system controller 410.

In an alternative embodiment, the system determines sleep based on the number of cycles that the eyelid(s) remain close. The system would reset a counter, for example, a register, to zero or one, depending upon the implementation, once the eyelid(s) is detected as close. For each cycle that the eyelid(s) remains closed, the counter is incremented by one. When the counter reaches a predetermined threshold, the determination is made that the wearer is asleep. Conversely, the counter could be reset to a number equal to the threshold value and decrement for each cycle that the eyelid(s) remain closed until the counter reaches zero or one, depending upon the implementation used.

Figure 7:
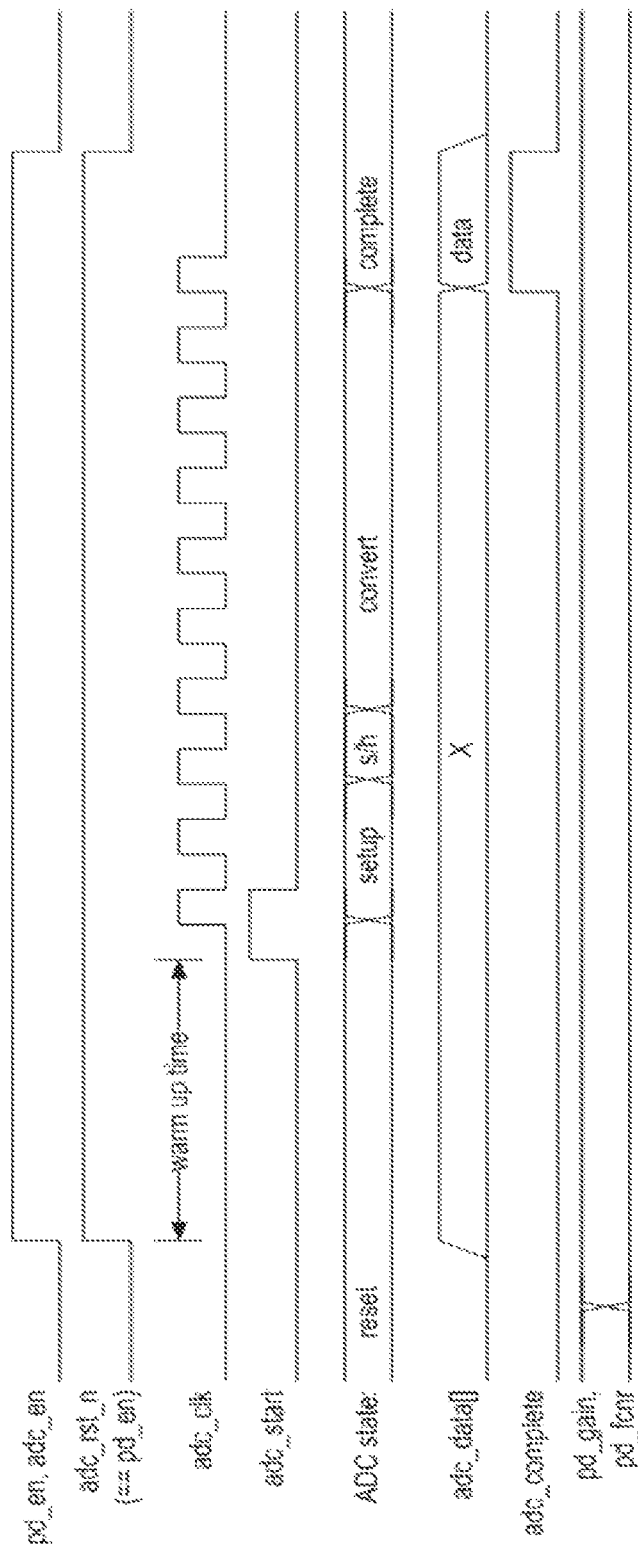
FIG. 7 illustrates a timing diagram in accordance with at least one embodiment of the present invention.

FIG. 7 illustrates a timing diagram of the control signals provided from a detection subsystem to an ADC 408 (FIG. 4) used in a photodetection signal path. The enable and clock signals adc_en, adc_rst_n and adc_clk are activated at the start of a sample sequence and continue until the analog-to-digital conversion process is complete. In one embodiment the ADC conversion process is started when a pulse is provided on the adc_start signal. The ADC output value is held in an adc_data signal and completion of the process is indicated by the analog-to-digital converter logic on an adc_complete signal. Also illustrated in FIG. 7 is the pd_gain signal which is utilized to set the gain of the amplifiers before the ADC. This signal is shown as being set before the warm-up time to allow the analog circuit bias and signal levels to stabilize prior to conversion.

Figure 8A:
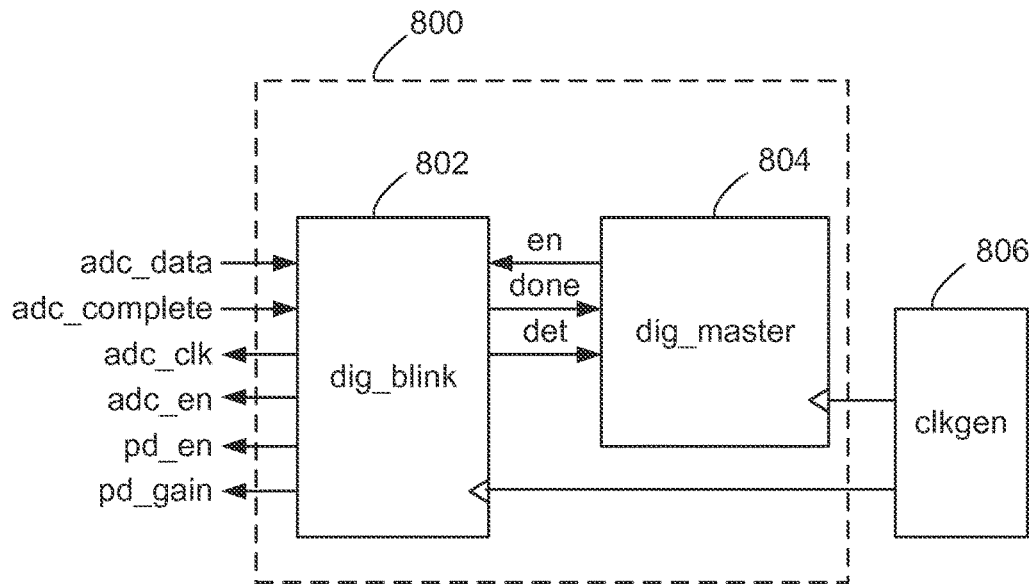
FIGS. 8A and 8B illustrate diagrammatic representations of digital system controllers in accordance with at least one embodiment of the present invention.

FIG. 8A illustrates a digital system controller 800 having a digital blink detection subsystem dig_blink 802. The digital blink detection subsystem dig_blink 802 may be controlled by a master state machine dig_master 804 and may be adapted to receive clock signals from a clock generator clkgen 806 external to the digital system controller 800. The digital blink detection subsystem dig_blink 802 may be adapted to provide control signals to and receive signals from a photodetection subsystem as described above. The digital blink detection subsystem dig_blink 802 may include digital conditioning logic and digital detection logic as described above, in addition to a state machine to control the sequence of operations in a blink detection algorithm. The digital blink detection subsystem dig_blink 802 may be adapted to receive an enable signal from the master state machine 804 and to provide a completion or done indication and a blink detection indication back to the master state machine 804. In at least one embodiment, the blink detection provides an indication when the wearer is drowsy as referenced previously. In at least one embodiment, the blink data is stored in a buffer such that upon detection of sleep by the system, the data in the buffer may be transferred and stored in memory for later analysis, for example, correlations between being overly attentive prior to sleep and poor sleep quality.

Figure 8B:
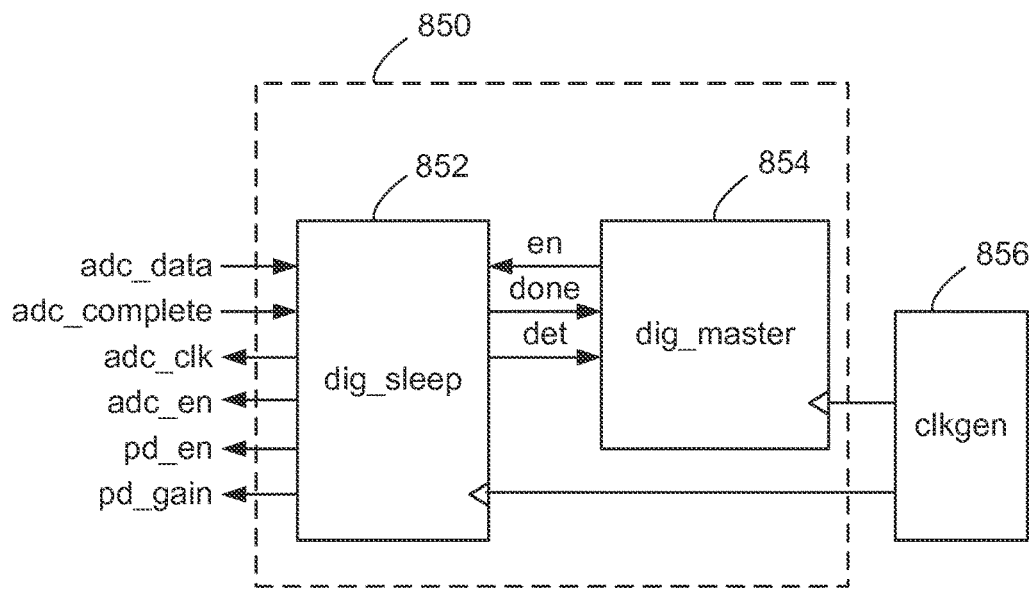

In an alternative embodiment, FIG. 8B illustrates a digital system controller 850 comprising a digital sleep detection subsystem dig_sleep 852. The digital sleep detection subsystem dig_sleep 852 may be controlled by a master state machine dig_master 854 and may be adapted to receive clock signals from a clock generator clkgen 856 external to the digital system controller 850. The digital sleep detection subsystem dig_sleep 852 may be adapted to provide control signals to and receive signals from a photodetection subsystem as described above. The digital sleep detection subsystem dig_sleep 852 may include digital conditioning logic and digital detection logic as described above, in addition to a state machine to control the sequence of operations in a sleep detection algorithm. The digital sleep detection subsystem dig_sleep 852 may be adapted to receive an enable signal from the master state machine 854 and to provide a completion or done indication and a sleep detection indication back to the master state machine 854.

In an alternative embodiment to either of the embodiments illustrated in FIGS. 8A and 8B, a time clock is connected to the clock generator 806 to track time since the lens began operation and provide a time stamp signal to the data manager in an embodiment where the data manager records data regarding the initiation and termination of sleep by the wearer such that when data is transmitted (or sent) from the lens to an external device using, for example, at least one electronic communication component, the external device is able to determine what time periods the wearer was asleep while wearing the lens by reverse calculating the time of day based on the time stamp from the lens and the current time on the external device when the data is transmitted as compared to the logged time stamps.

Figure 9A:
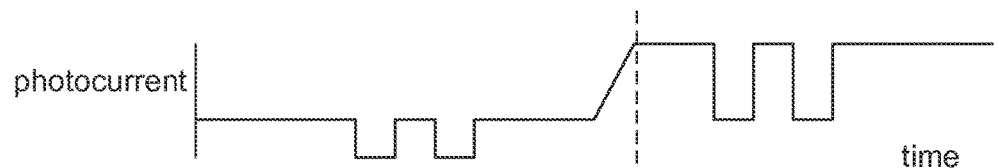
FIGS. 9A through 9G illustrate timing diagrams for automatic gain control in accordance with at least one embodiment of the present invention.
Figure 9B:
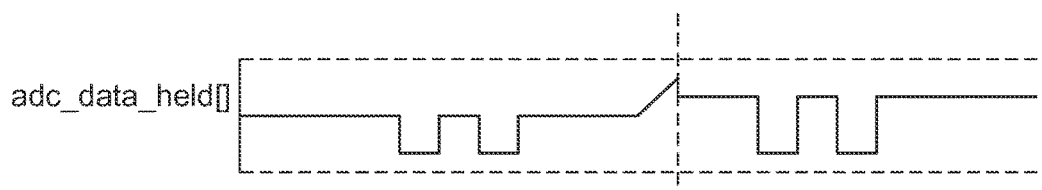
Figure 9C:
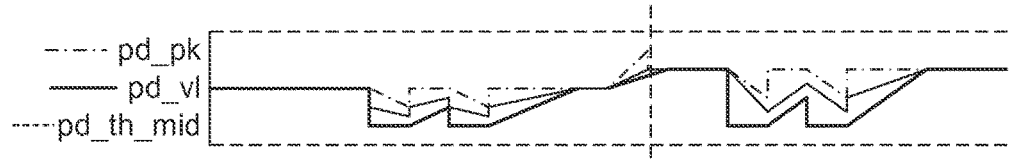
Figure 9D:
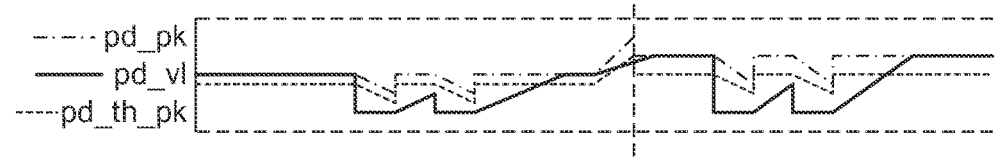
Figure 9E:
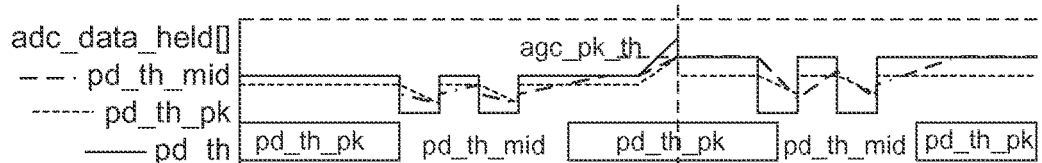
Figure 9F:
Figure 9G:

FIGS. 9A-9G depict waveforms to illustrate the operation of the threshold generation circuit and automatic gain control (FIG. 5). FIG. 9A illustrates an example of photocurrent versus time as might be provided by a photodiode in response to varying light levels. In the first portion of the plot, the light level and resulting photocurrent are relatively low compared to in the second portion of the plot. In both the first and second portions of the plot a double blink is seen to reduce the light and photocurrent. Note that the attenuation of light by the eyelid may not be one hundred (100) percent, but a lower value depending on the transmission properties of the eyelid for the wavelengths of light incident on the eye. FIG. 9B illustrates the adc_data_held value that is captured in response to the photocurrent waveform of FIG. 9A. For simplicity, the adc_data_held value is illustrated as a continuous analog signal rather than a series of discrete digital samples. It will be appreciated that the digital sample values will correspond to the level illustrated in FIG. 9B at the corresponding sample times. The dashed lines at the top and bottom of the plot indicate the maximum and minimum values of the adc_data and adc_data_held signals. The range of values between the minimum and maximum is also known as the dynamic range of the adc_data signal. As discussed below, the photodetection signal path gain is different (lower) in the second portion of the plot. In general the adc_data_held value is directly proportional to the photocurrent, and the gain changes only affect the ration or the constant of proportionality. FIG. 9C illustrates the pd_pk, pd_vl and pd_th_mid values calculated in response to the adc_data_held value by the threshold generation circuit. FIG. 9D illustrates the pd_pk, pd_vl and pd_th_pk values calculated in response to the adc_data_held value in some embodiments of the threshold generation circuit. Note that the pd_th_pk value is always some proportion of the pd_pk value. FIG. 9E illustrates the adc_data_held value with the pd_th_mid and pd_th_pk values. Note that during long periods of time where the adc_data_held value is relatively constant the pd_th_mid value becomes equal to the adc_data_held value as the pd_vl value decays to the same level. The pd_th_pk value always remains some amount below the adc_data_held value. Also illustrated in FIG. 9E is the selection of pd_th where the pd_th value is selected to be the lower of pd_th_pk and pd_th_mid. In this way the threshold is always set some distance away from the pd_pk value, avoiding false transitions on pd_data due to noise on the photocurrent and adc_data held signals. FIG. 9F illustrates the pd_data value generated by comparison of the adc_data_held value to the pd_th value. Note that the pd_data signal is a two-valued signal which is low when a blink is occurring. FIG. 9G illustrates a value of tia_gain versus time for these example waveforms. The value of tia_gain is set lower when the pd_th starts to exceed a high threshold shown as agc_pk_th in FIG. 9E. It will be appreciated that similar behavior occurs for raising tia_gain when pd_th starts to fall below a low threshold. Looking again at the second portion of each of the FIGS. 9A through 9E the effect of the lower tia_gain is clear. In particular note that the adc_data_held value is maintained near the middle of the dynamic range of the adc_data and adc_data_held signals. Further, it is important to note that the pd_pk and pd_vl values are updated in accordance with the gain change as described above such that discontinuities are avoided in the peak and valley detector states and values due solely to changes in the photodetection signal path gain.

Figure 10:
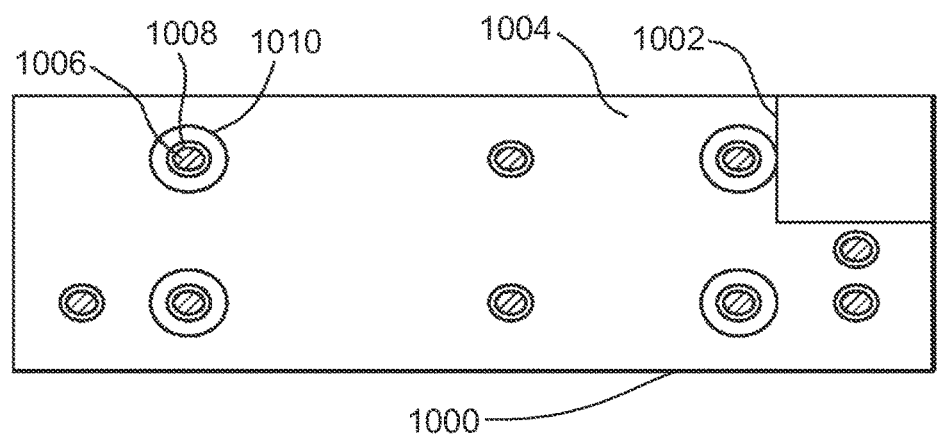
FIG. 10 illustrates a diagrammatic representation of light-blocking and light-passing regions on an integrated circuit die in accordance with at least one embodiment of the present invention.

FIG. 10 illustrates light-blocking and light-passing features on an integrated circuit die 1000. The integrated circuit die 1000 includes a light passing region 1002, a light blocking region 1004, bond pads 1006, passivation openings 1008, and light blocking layer openings 1010. The light-passing region 1002 is located above the photosensors (not illustrated), for example, an array of photodiodes implemented in the semiconductor process. In at least one embodiment, the light-passing region 1002 permits as much light as possible to reach the photosensors thereby maximizing sensitivity. This may be done through removing polysilicon, metal, oxide, nitride, polyimide, and other layers above the photoreceptors, as permitted in the semiconductor process utilized for fabrication or in post-processing. The light-passing area 1002 may also receive other special processing to optimize light detection, for example, an anti-reflective coating, filter, and/or diffuser. The light-blocking region 1004 may cover other circuitry on the die which does not require light exposure. The performance of the other circuitry may be degraded by photocurrents, for example, shifting bias voltages and oscillator frequencies in the ultra-low current circuits required for incorporation into contact lenses, as mentioned previously. The light-blocking region 1004 is formed with a thin, opaque, reflective material, for example aluminum or copper already used in semiconductor wafer processing and post-processing. If implemented with metal, the material forming the light-blocking region 1004 must be insulated from the circuits underneath and the bond pads 1006 to prevent short-circuit conditions. Such insulation may be provided by the passivation already present on the die as part of normal wafer passivation, e.g. oxide, nitride, and/or polyimide, or with other dielectric added during post-processing. Masking permits light blocking layer openings 1010 so that conductive light-blocking metal does not overlap bond pads on the die. The light-blocking region 1004 is covered with additional dielectric or passivation to protect the die and avoid short-circuits during die attachment. This final passivation has passivation openings 1008 to permit connection to the bond pads 1006.

In an alternative embodiment where the contact lens includes tinting capabilities, the light-passing region 1002 is at least partially overlapping with the region of the contact lens capable of being tinted. Where the photosensors are present in both the tinting region and non-tinting regions of the contact lens, it allows for a determination of the amount of light being blocked by the tinting. In a further embodiment, the entire light-passing region 1002 is present in the tinting region.

Figure 11:
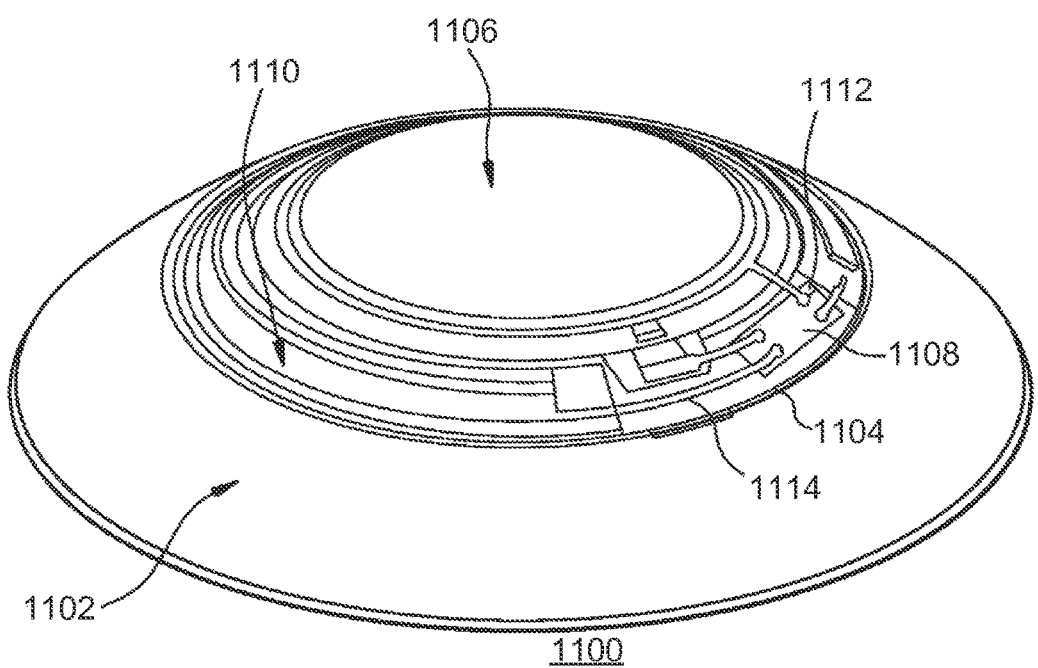
FIG. 11 illustrates a diagrammatic representation of an electronic insert, including a blink detector, for a powered contact lens in accordance with at least one embodiment of the present invention.

FIG. 11 illustrates a contact lens with an electronic insert having an eyelid position sensor system in accordance with the present embodiments (invention). The contact lens 1100 includes a soft plastic portion 1102 which provides an electronic insert 1104. This insert 1104 includes a lens 1106 which is activated by the electronics, for example, focusing near or far depending on activation. In the illustrated embodiment, integrated circuit 1108 mounts onto the insert 1104 and connects to batteries 1110, lens 1106, and other components as necessary for the system. The integrated circuit 1108 includes a photosensor 1112 and associated photodetector signal path circuits. The photosensor 1112 faces outward through the lens insert and away from the eye, and is thus able to receive ambient light. The photosensor 1112 may be implemented on the integrated circuit 1108 (as shown), for example, as a single photodiode or array of photodiodes. The photosensor 1112 may also be implemented as a separate device mounted on the insert 1104 and connected with wiring traces 1114. When the eyelid closes, the lens insert 1104 including photodetector 1112 is covered, thereby reducing the light level incident on the photodetector 1112. The photodetector 1112 is able to measure the ambient light to determine if the user is blinking or not. Based on this disclosure one of ordinary skill in the art should appreciate that photodetector 112 may be replaced or augmented by the other sensors discussed in this disclosure.

Additional embodiments of the blink detection method may allow for more variation in the duration and spacing of the blink sequence, for example, by timing the start of a second blink based on the measured ending time of a first blink rather than by using a fixed template or by widening the mask "don't care" intervals (0 values).

It will be appreciated that blink detection and/or sleep detection may be implemented in digital logic or in software running on a microcontroller. The algorithm logic or microcontroller may be implemented in a single application-specific integrated circuit, ASIC, with photodetection signal path circuitry and a system controller, or it may be partitioned across more than one integrated circuit.

It is known that the eyelids protect the globe in a number of ways, including the blink reflex and the tear spreading action. The blink reflex of the eyelids prevents trauma to the globe by rapidly closing upon a perceived threat to the eye. Blinking also spreads tears over the globe's surface to keep it moist and rinse away bacteria and other foreign matter. But the movement of the eyelids may also indicate other actions or functions at play beyond being used to track when an individual (or wearer) wearing an electronic ophthalmic lens has fallen asleep. It is also important to note that the sensed data, in addition to or in alternate use may simply be utilized as part of a triggering event rather than as a collection process. In other words, it should also be appreciated that a device utilizing such a sensor may not change state in a manner visible to the user; rather the device may simply log data.

Figure 12A:
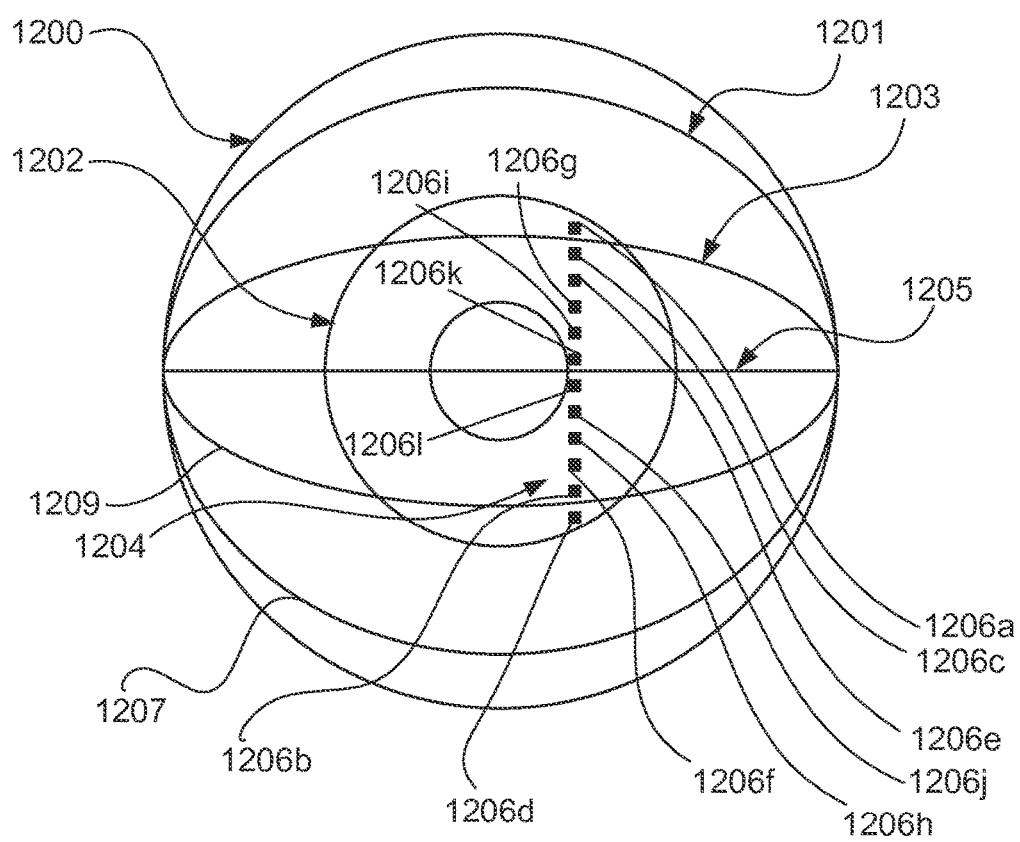
FIGS. 12A and 12B illustrate diagrammatic representations of eyelid position sensors in accordance with at least one embodiment of the present invention.
Figure 12B:
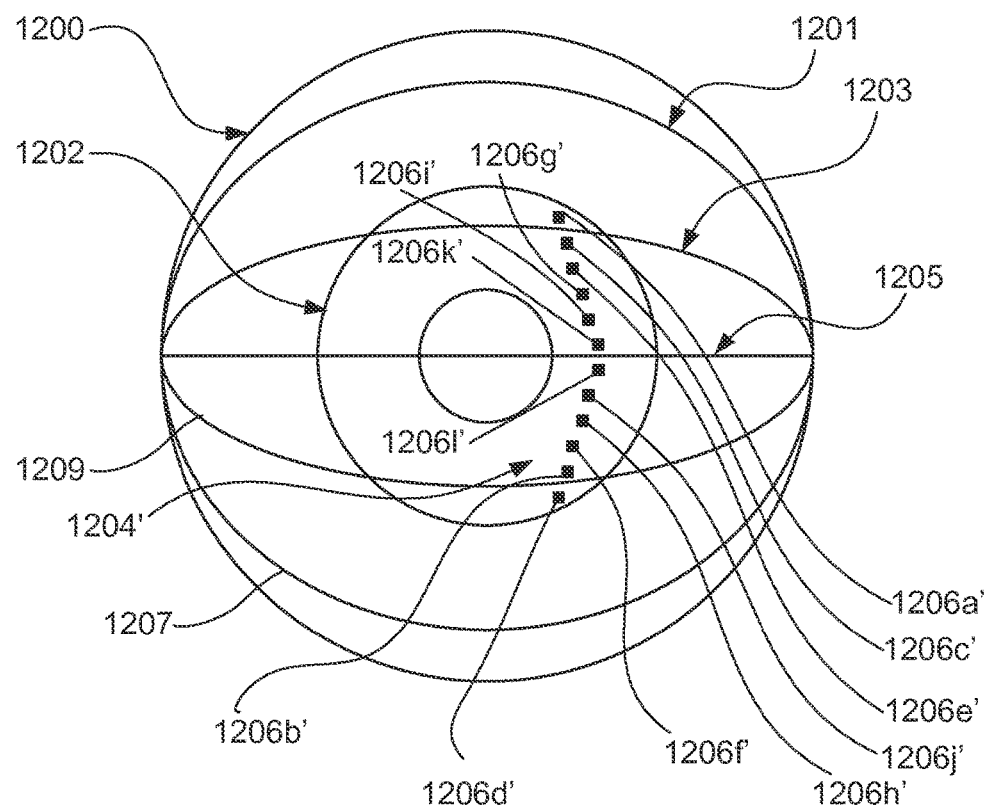

Referring now to FIG. 12A, there is illustrated an eyelid position sensor system on an eye 1200. The system is incorporated into a contact lens 1202. The top and bottom eyelids are shown, with the top eyelid having possible locations 1201, 1203, and 1205 in order of increasing closure. The bottom eyelid is also illustrated with levels of closure corresponding to the top eyelid; namely, locations 1207, 1209 and 1205. When the eyelids are closed, they occupy the same position; namely, 1205. The contact lens 1202 in accordance with the embodiment includes a sensor array 1204. This sensor array 1204 includes one or more photosensors. In this embodiment, the sensor array 1204 includes twelve (12) photosensors 1206a-1206l. With the top eyelid at position 1201 and the bottom eyelid at position 1207, all photosensors 1206a-1206l are exposed and receive ambient light, thereby creating a photocurrent which may be detected by an electronic circuit described herein. With the eyelids partially closed at positions 1203 and 1209, the top and bottom photosensors 1206a and 1206b are covered, receive less light than the other photosensors 1206c-1206l, and output a correspondingly lower current which may be detected by the electronic circuit. With the eyelids totally closed in position 1205, all sensors 1206a-1206l are covered with a corresponding reduction in current. This system may be used to detect eyelid position by sampling each photosensor in the sensor array and using the photocurrent output versus sensor position to determine eyelid position, for example, if the upper and lower eyelids do not fully open after blinks indicating potential onset of sleep or fatigue. It will be appreciated that the photosensors should be placed in suitable locations on the contact lens, for example, providing enough sample locations to reliably determine eyelid position while not obstructing the clear optic zone (roughly the area occupied by a dilated pupil.) This system may also be used to detect blinks by routinely sampling the sensors and comparing measurements over time. In an alternative embodiment, photosensors 1206a'-1206l' of a sensor array 1204' form an arcuate pattern around the pupil while being vertically spaced from each other as illustrated, for example, in FIG. 12B. Under either of the illustrated embodiment, one of ordinary skill in the art should appreciate that a number other than 12 may be used in the sensor array. Further examples include a number in a range of 3 through 15 (including the end points in at least one embodiment), and more particularly a number in a range of 4 through 8 (including the end points in at least one embodiment).

Figure 13A:
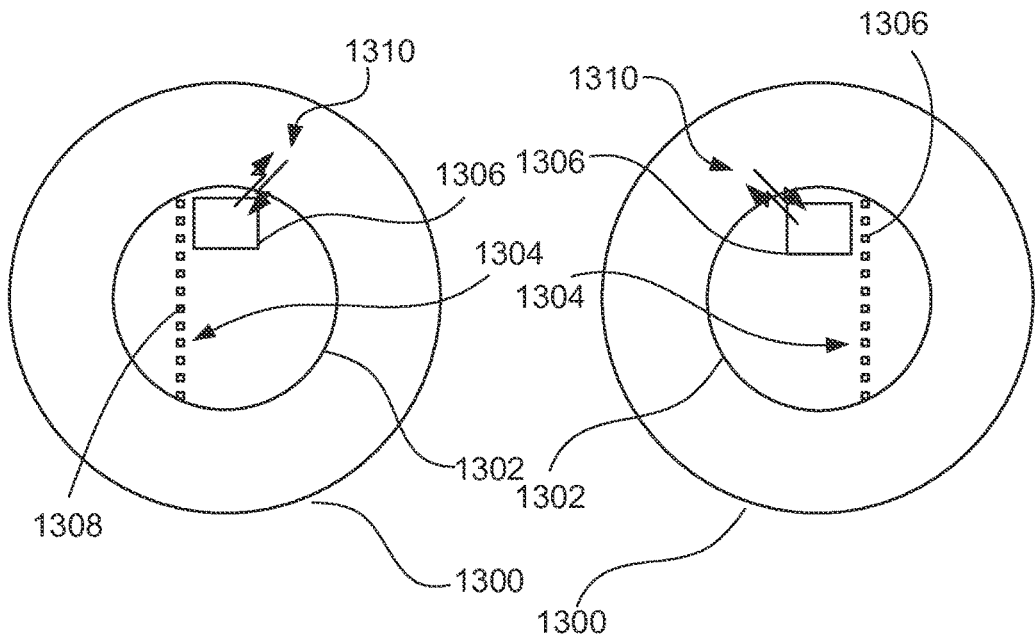
FIG. 13A illustrates a diagrammatic representation of two eyelid position sensors having a communication channel for synchronizing operation between two eyes in accordance with at least one embodiment of the present invention.

FIG. 13A illustrates a system in which two eyes 1300 are at least partially covered with contact lenses 1302. Sensor arrays 1304 are present in both of the contact lenses 1302 to determine eyelid position, as previously described with respect to FIG. 12A. In this embodiment, the contact lenses 1302 each have an electronic communication component 1306. Electronic communication component 1306 in each contact lens 1302 permits two-way communication to take place between the contact lenses 1302. The electronic communication components 1306 may include radio frequency (RF) transceivers, antennas, interface circuitry for photosensors 1308, and associated or similar electronic components. The communication channel represented by line 1310 may be RF transmissions at the appropriate frequency and power with an appropriate data protocol to permit effective communication between the contact lenses 1302. Transmission of data between the two contact lenses 1302 may, for example, verify that both eyelids have closed in order to detect a true, purposeful eyelid closure rather than a wink, involuntary blink, or squinting with one eye. The transmission may also allow a system to determine if both eyelids have closed by a similar amount, for example, that which is associated with a user reading up-close. Data transmission may also take place to an external device, for example, spectacle glasses, a patch worn on the user's temple, or a smartphone (or other processor based system). In at least one embodiment, the electronic communication components allow for the transmission of logged sleep data to the smartphone (or other external device). As such the electronic communication components 1306 may be present on just one lens in at least one alternative embodiment. In an alternative embodiment, an accelerometer present in the smartphone (or other accelerometer equipped device with transmission capability) worn by the individual provides movement data for use in crosschecking a sleep determination such as a lack of general movement is indicative of the possibility of sleep or data indicative of the individual being stationary.

Figure 13B:
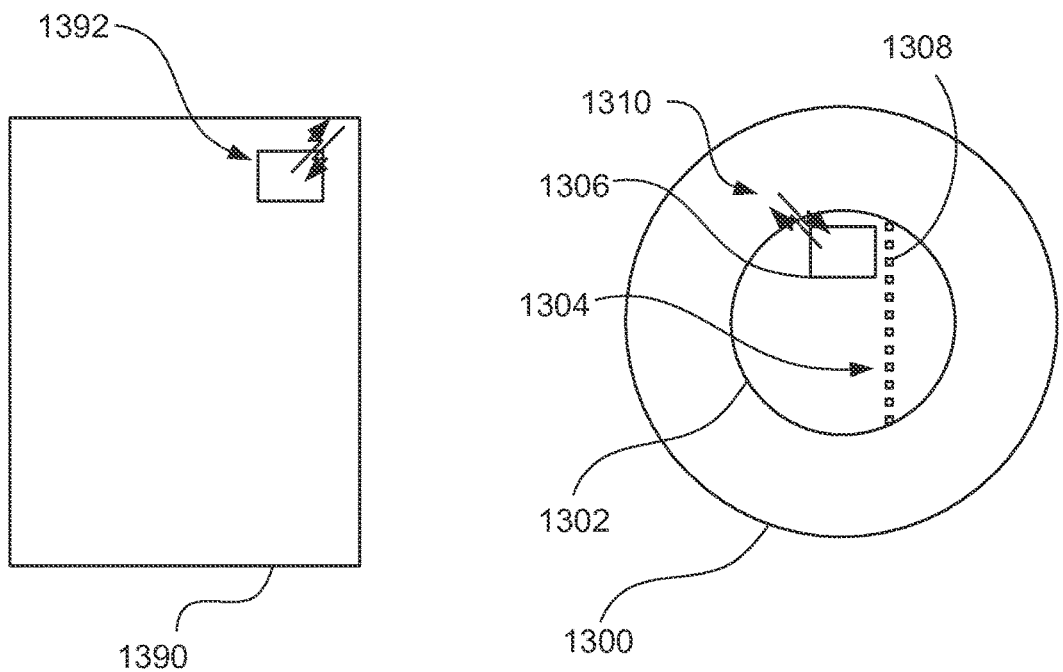
FIG. 13B illustrates a diagrammatic representation of one eyelid position sensor having a communication channel for communicating with an external device in accordance with at least one embodiment of the present invention.

In an alternative embodiment, the external device 1390, illustrated in FIG. 13B, receives and stores data relating to sleep as determined by the contact lens 1300 through at least one electronic communication component 1392, which allows for communication with the electronic communication component 1306 on the contact lens 1300. One advantage to using an external device is that the external device may keep track of time more accurately than the contact lens while providing sufficient memory for a faster sampling rate without concern of filling up memory on the contact lens. More accurate time keeping will provide a data set allowing for more accurate analysis.

In a further or alternative embodiment, the external device provides a mechanism for the wearer to indicate when to initiate a sleep study and/or termination of the sleep study. One example is by displaying a graphical user interface on the external device that includes a virtual button to be touched by the user.

Figure 14A:
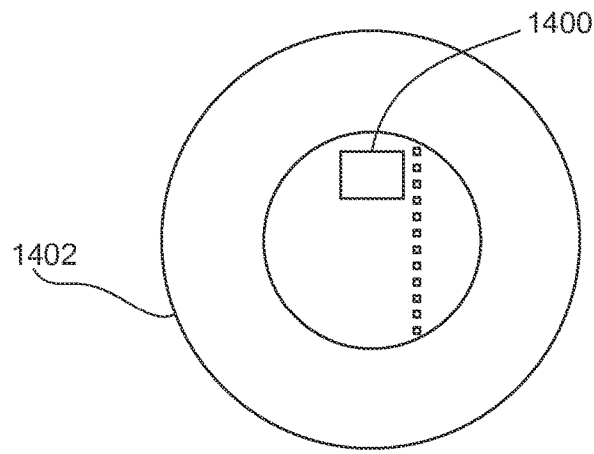
FIG. 14A illustrates a diagrammatic representation of an electronic system incorporated into a contact lens for detecting eyelid position in accordance with at least one embodiment of the present invention.
Figure 14B:
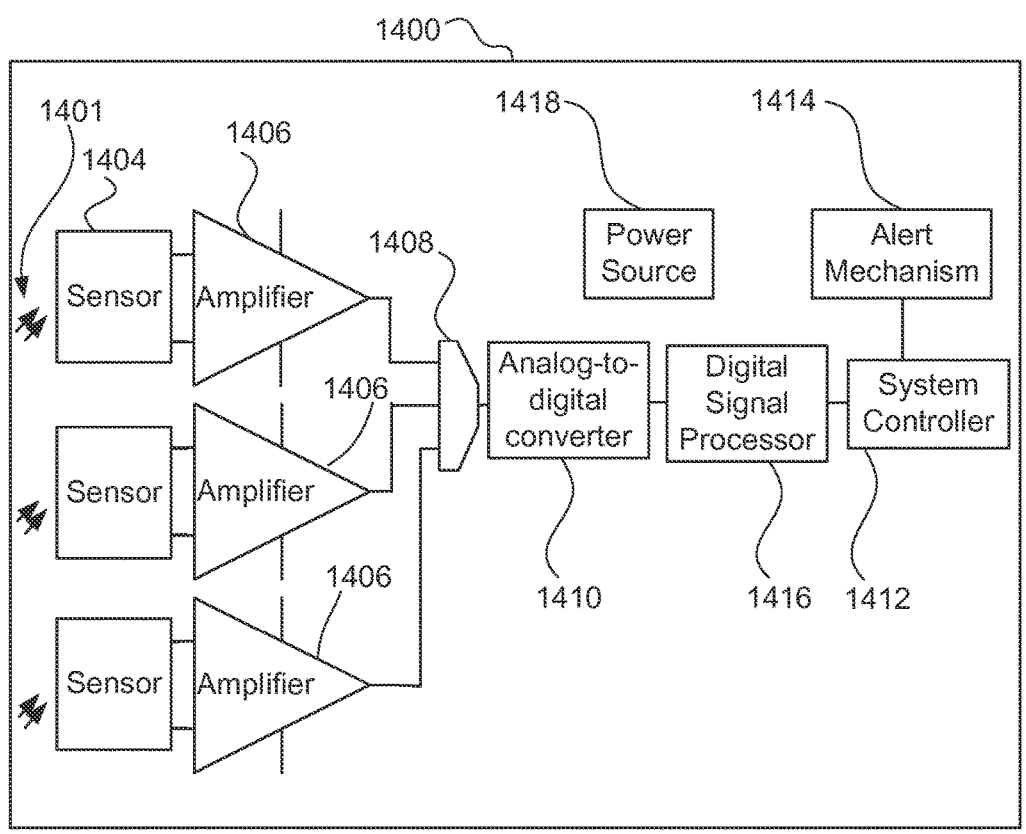
FIG. 14B illustrates an enlarged view of the electronic system of FIG. 14A.

FIGS. 14A and 14B illustrate an electronic system 1400 in which eyelid position photosensors, as set forth above, are used to trigger activity in a contact lens 1402 or more specifically, a powered or electronic ophthalmic lens. FIG. 14A shows the electronic system 1400 on the lens 1402, and FIG. 14B is an exploded view of the system 1400. Light 1401 is incident onto one or more photosensors 1404 as previously described with respect to FIG. 12. These photosensors 1404 may be implemented with photodiodes, cadmium sulfide (CdS) sensors, or other technologies suitable for converting ambient light into current. Depending on the choice of photosensors 1404, amplifiers 1406 or other suitable circuitry may be required to condition the input signals for use by subsequent or downstream circuits. A multiplexer 1408 permits a single analog-to-digital converter (or ADC) 1410 to accept inputs from multiple photosensors 1404. The multiplexer 1408 may be placed immediately after the photosensors 1404, before the amplifiers 1406, or may not be used depending on considerations for current consumption, die size, and design complexity. Since multiple photosensors 1404 are needed at various positions on the eye to detect eyelid position, sharing downstream processing components (for example amplifiers, an analog-to-digital converter, and digital signed processors) may significantly reduce the size needed for the electronic circuitry. The amplifiers 1406 create an output proportional to the input, with gain, and may function as transimpedance amplifiers which convert input current into output voltage. The amplifiers 1406 may amplify a signal to a usable level for the remainder of the system, such as giving the signal enough voltage and power to be acquired by the ADC 1410. For example, the amplifiers 1406 may be necessary to drive subsequent blocks since the output of the photosensors 1404 may be quite small and may be used in low-light environments. Amplifiers 1406 may also be implemented as variable-gain amplifiers, the gain of which may be adjusted by a system controller 1412 to maximize the dynamic range of the system 1400. In addition to providing gain, the amplifiers 1406 may include other analog signal conditioning circuitry, such as filtering and other circuitry appropriate to the photosensor 1404 and amplifier 1406 output. The amplifiers 1406 may be any suitable device for amplifying and conditioning the signal output by the photosensor 1404. For example, the amplifiers 1404 may simply be a single operational amplifier or a more complicated circuit comprising one or more operational amplifiers.

As set forth above, the photosensors 1404 and the amplifiers 1406 are configured to detect incident light 1401 at various positions on the eye and convert the input current into a digital signal usable ultimately by the system controller 1412. In at least one embodiment, the system controller 1412 is preprogrammed to sample each photosensor 1404 on the eye to detect eyelid position and provide an appropriate output signal to data manager 1414. The system controller 1412 also includes associated memory. The system controller 1412 may combine recent samples of the photosensors 1404 to preprogrammed patterns correlating to eyelid open and squinting positions. For example, when the pattern matches that of both eyelids partially closing associated with fatigue, the system controller 1412 may trigger the data manager 1414 to log data. Recording a user's eyelid patterns under various ambient light and focal distance situations may be required to program the system controller 1412 for reliable detection. The system 1400 may need to differentiate between eyelid position changes, normal changes in ambient light, shadows, and other phenomena. This differentiation may be accomplished through proper selection of the sampling frequency, amplifier gain, and other system parameters, optimization of sensors placement in the contact lens, determination of eyelid position patterns, recording ambient light, comparing each photosensor to adjacent and all photosensors, and other techniques to discern eyelid position uniquely.

In this embodiment, the ADC 1410 may be used to convert a continuous, analog signal output from the amplifiers 1406 through the multiplexer into a sampled, digital signal appropriate for further signal processing. For example, the ADC 1410 may convert an analog signal output from the amplifiers 1406 into a digital signal that may be useable by subsequent or downstream circuits, such as a digital signal processing system or microprocessor 1416. A digital signal processing system or digital signal processor 1416 may be utilized for digital signal processing, including one or more of filtering, processing, detecting, and otherwise manipulating/processing sampled data to permit incident light detection for downstream use. The digital signal processor 1416 may be preprogrammed with various eyelid position and/or closure patterns. The digital signal processor 1416 also includes associated memory in at least one embodiment. The digital signal processor 1416 may be implemented utilizing analog circuitry, digital circuitry, software, and/or a combination thereof. The ADC 1410 along with the associated amplifiers 1406 and digital signal processor 1416 are activated at a suitable rate in agreement with the sampling rate previously described, for example, every one hundred (100) ms.

A power source 1418 supplies power for numerous components including the eyelid position sensor system 1400. The power source 1418 may also be utilized to supply power to other components on the contact lens. The power may be supplied from a battery, energy harvester, or other suitable means as is known to one of ordinary skill in the art. Essentially, any type of power source 1418 may be utilized to provide reliable power for all other components of the system. An eyelid position sensor array pattern, processed from analog to digital, may enable activation of the system controller 1412 or a portion of the system controller 1412. Furthermore, the system controller 1412 may control other aspects of a powered contact lens depending on input from the digital signal processor 1408, for example, activating the data manager 1414.

Figure 15:
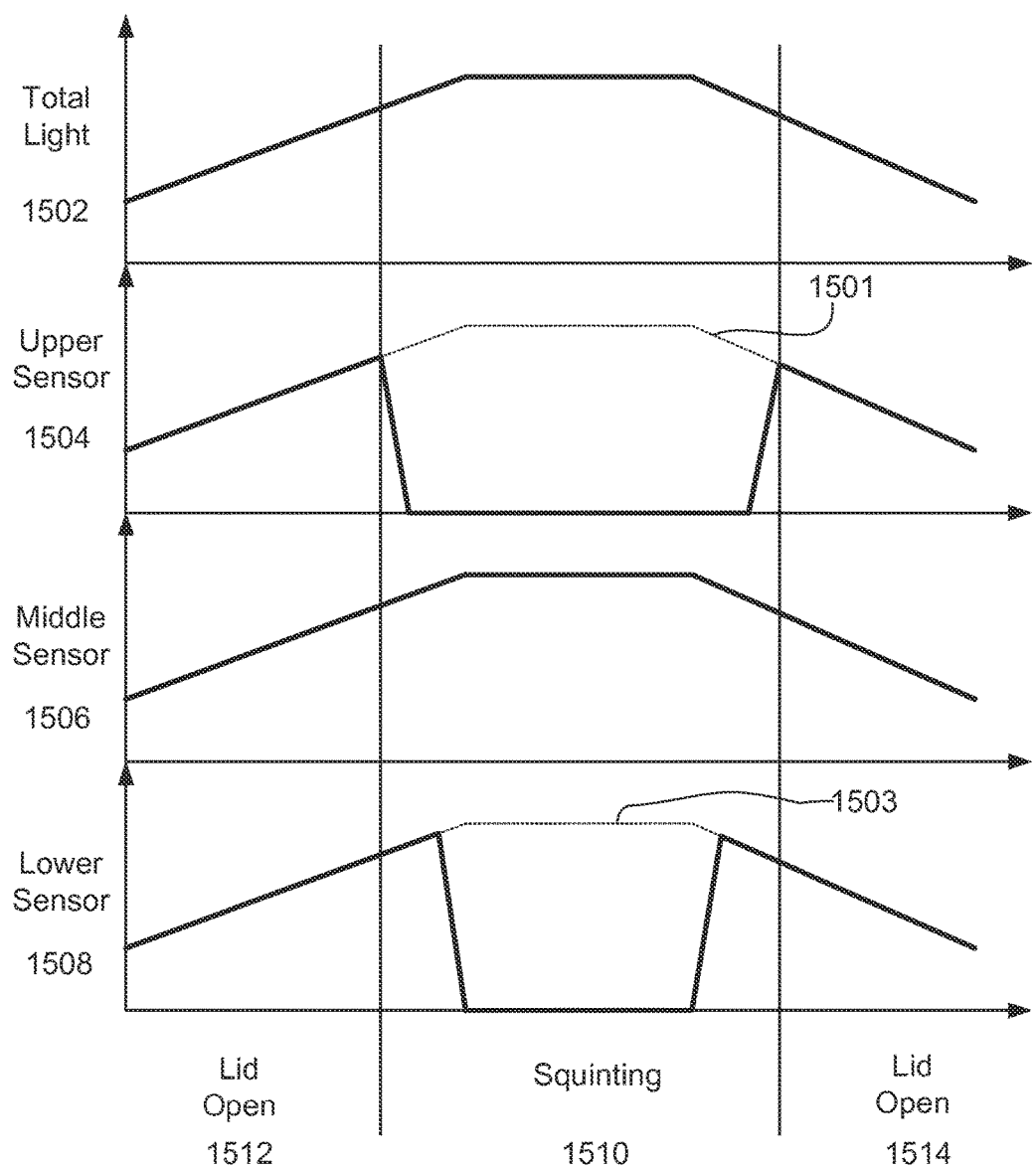
FIG. 15 illustrates a diagrammatic representation of outputs from eyelid position sensors in accordance with at least one embodiment of the present invention.

Referring now to FIG. 15 there is illustrated an output characteristic for three photosensors positioned at three different vertical positions on the contact lens. The output characteristics may represent the current proportional to incident light on each photosensor or may represent a downstream signal, for example, digital sampled data values versus time at the output of the ADC (element 1410 in FIG. 14B). Total incident light 1502 increases, holds steady, and then decreases, for example, when walking from a dark room to a bright hallway then back to a dark room. All three photosensors 1504, 1506, and 1508 would output a signal similar to that of the ambient light if the eyelid remained open, illustrated by dotted lines 1501 and 1503 for photosensors 1504 and 1508. In addition to the ambient light level 1502 changing, partial closure of the eyelids is indicated by position 1510, different than that of the lid open positions 1512 and 1514. When the lid partially closes, upper photosensor 1504 becomes covered by the upper eyelid and outputs a correspondingly lower level due to obstruction of the photosensor by the eyelid. Despite ambient light 1502 increasing, photosensor 1504 receives less light and outputs a lower signal due to the partially closed eyelid. A similar response is observed with photosensor 1508 which becomes covered. Middle sensor 1506 is not covered during squinting and thus continues to see the light level increase, with a corresponding increase in output level. While this example illustrates one particular case, it should be apparent how various configurations of sensor position and eyelid movement could be detected.

Figure 16A:
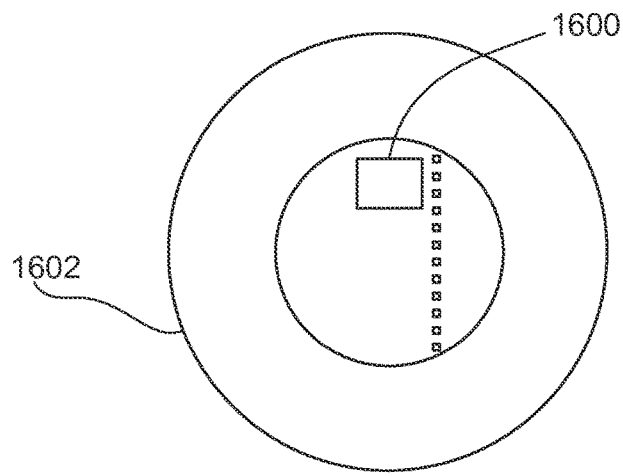
FIG. 16A illustrates a diagrammatic representation of another electronic system incorporated into a contact lens for detecting eyelid position in accordance with at least one embodiment of the present invention.
Figure 16B:
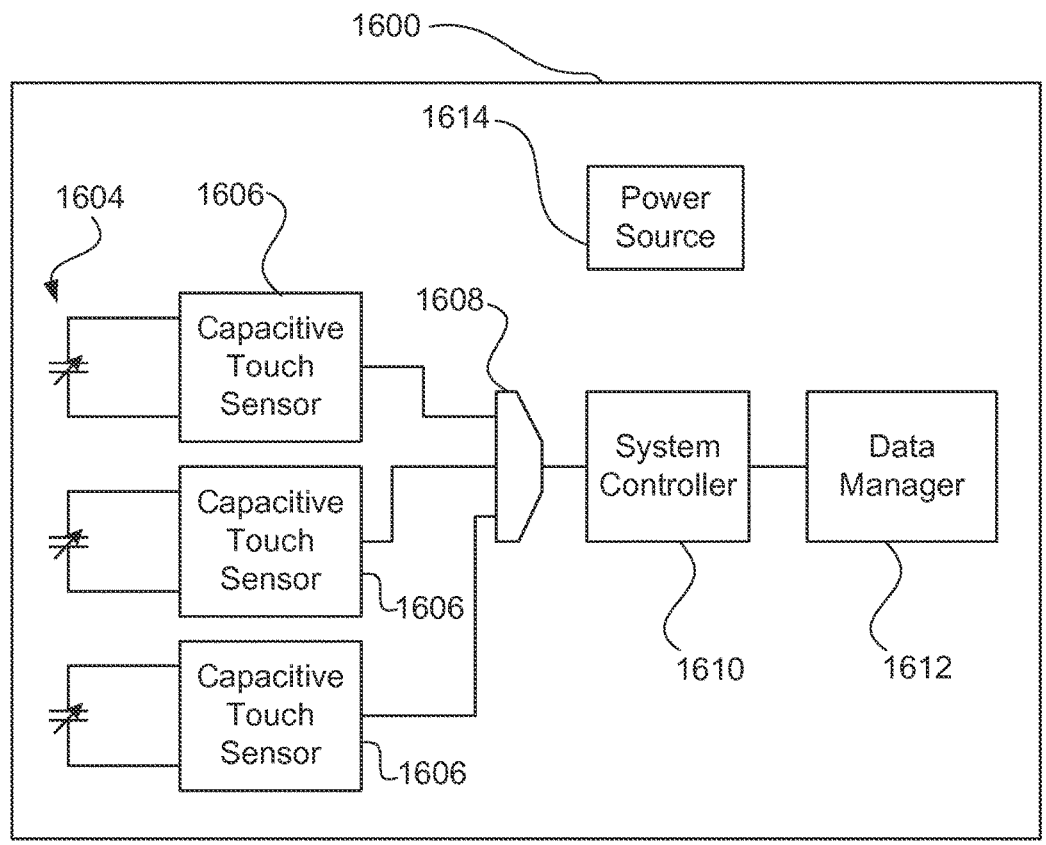
FIG. 16B illustrates an enlarged view of the electronic system of FIG. 16A.

FIGS. 16A and 16B illustrate an alternate detection system 1600 incorporated into a contact lens 1602. FIG. 16A illustrates the system 1600 on the contact lens 1602 and FIG. 16B illustrates an exploded view of the system 1600. In this embodiment, capacitive touch sensors 1604 are utilized instead of photosensors. In an alternative embodiment, capacitive touch sensors 1604 are utilized in addition to photosensors. Capacitive touch sensors are common in the electronics industry, for example, in touch-screen displays. The basic principle is that a variable capacitor 1604 is implemented in a physical manner such that the capacitance varies with proximity or touch, for example, by implementing a grid covered by a dielectric. Sensor conditioners 1606 create an output signal proportional to the capacitance, for example, by measuring the change in an oscillator having the variable capacitor or by sensing the ratio of the variable capacitor to a fixed capacitor with a fixed-frequency AC signal. The output of the sensor conditioners 1606 may be combined with a multiplexer 1608 to reduce downstream circuitry. In this embodiment, the signal conditioning circuitry as described above with respect to FIG. 14 is omitted for simplicity. A system controller 1610 receives inputs from the capacitance sensor conditioner 1606 via the multiplexor 1608, for example, by activating each sensor in order and recording the values. It may then compare measured values to pre-programmed patterns and historical samples to determine lid position. The capacitor touch sensors 1604 may be laid out in a physical pattern similar to that previously described for the photodetectors, but would be optimized for detecting changes in capacitance with lid position. The sensors, and for that matter the whole electronic system, would be encapsulated and insulated from the saline contact lens environment. As the eyelid covers a sensor 1604, the change in capacitance would be detected rather than the change in ambient light previously described. FIG. 16B also illustrates the inclusion of a power source 1614 in at least one embodiment.

It is important to note that ADC's and digital signal processing circuitry may be utilized in accordance with the capacitive touch sensors if needed as illustrated with respect to the photosensors of FIG. 14B. In an alternative embodiment, the capacitive touch sensors are any pressure sensor. In a further embodiment, there is a combination of photosensors and pressure sensors on the lens.

FIGS. 17A-17D illustrate an alternative embodiment where the eyelid position sensor system is a sensor having a strip that covers a plurality of vertical points along the contact lens 1702 that works in conjunction with circuit 1700. One example of a sensor that may have a strip configuration is a capacitance sensor. FIG. 17A illustrates an example where the strip 1708 is substantially straight on the contact lens 1702. Although the strip 1708 is illustrated as being orientated parallel to a line bisecting the contact lens 1702, it may have an angled orientation relative to the bisecting line or have an arcuate shape. FIG. 17B illustrates an example where the strip 1708a takes a serpentine path along the contact lens 1702. In the embodiment illustrated in FIG. 17C, the serpentine configuration of strip 1708b will increase the change in capacitance detected by the circuit 1700 as the eyelid approaches a closed state. The level of capacitance change will translate to the amount of eyelid closure. Another example of a sensor that may have a strip configuration is a piezoelectric pressure transducer with a diaphragm and a base having a strip configuration. As the eyelids close, additional pressure will be applied by the eyelids against the piezoelectric pressure transducer thus allowing the ability to determine the level of eyelid closure. The continuous sensing along the vertical axis provides an improved granularity over a plurality of sensors thus providing improved measurement of the eyelid location. FIG. 17D illustrates an electrical circuit that can be used in conjunction with strip sensors 1708, 1708a, 1708b that includes a system controller 1710, a data manager 1712 and a power source 1714. In a further alternative embodiment, there are multiple strips present. An advantage of an angled and/or serpentine strip configuration is that lid position may still be detected even if the contact lens is orientated incorrectly on the wearer's eye.

The activities of the digital signal processing block and system controller (1416 and 1412 in FIG. 14B, respectively, system controller 1610 in FIG. 16B, and system controller 1710 in FIG. 17D) depend on the available sensor inputs, the environment, and user reactions. The inputs, reactions, and decision thresholds may be determined from one or more of ophthalmic research, pre-programming, training, and adaptive/learning algorithms. For example, the general characteristics of eyelid movement may be well-documented in literature, applicable to a broad population of users, and pre-programmed into system controller. However, an individual's deviations from the general expected response and/or changes in blink frequency may be recorded in a training session or part of an adaptive/learning algorithm which continues to refine the response in operation of the electronic ophthalmic device. In one embodiment, the user may train the device by activating a handheld fob, which communicates with the device, when the user desires near focus. A learning algorithm in the device may then reference sensor inputs in memory before and after the fob signal to refine internal decision algorithms. This training period could last for one day, after which the device would operate autonomously with only sensor inputs and not require the fob.

FIGS. 18A and 18B illustrate example eye movement sensor systems 1800 for detecting movement of the eye during, for example, sleep. Sensor 1802 detects the movement and/or position of the pupil or, more generally, the eye. The sensor 1802 may be implemented as a multi-axis accelerometer on a contact lens 1801. With the contact lens 1801 being affixed to the eye and generally moving with the eye, an accelerometer on the contact lens 1801 may track eye movement. It is important to note that any suitable device may be utilized as the sensor 1802, and more than a single sensor 1802 may be utilized. The output of the sensor 1802 is acquired, sampled, and conditioned by signal processor 1804. The signal processor 1804 may include any number of devices including an amplifier, a transimpedance amplifier, an analog-to-digital converter, a filter, a digital signal processor, and related circuitry to receive data from the sensor 1802 and generate output in a suitable format for the remainder of the components of the system 1800. The signal processor 1804 may be implemented utilizing analog circuitry, digital circuitry, software, and/or a combination thereof. In at least one embodiment, the signal processor 1804 and the sensor 1802 are fabricated on the same integrated circuit die. The sensor circuitry for acquisition and conditioning of an accelerometer is different than the circuitry for a muscle activity sensor or optical pupil tracker. The output of the signal processor 1804 in at least one embodiment is a sampled digital stream and may include absolute or relative position, movement, detected gaze in agreement with convergence, or other data. System controller 1806 receives input from the signal processor 1804 and uses this information, in conjunction with other inputs, to determine whether the wearer is asleep. System controller 1806 may both trigger the activity of sensor 1802 and the signal processor 1804 while receiving output from them. System controller 1806 uses input data from the signal processor 1804 and/or transceiver 1810 to decide if the wearer is lying down based on the orientation of the sensor 1802 based on orientation on an X, Y, and Z axes when no eye movement is detected. If the axes are as illustrated in FIG. 18C, then when the accelerometer detects stable acceleration in the X axis in either direction or in the Z axis in either direction, then the wearer's head has a horizontal orientation. When the accelerometer detects stable acceleration in the Y axis in the negative direction, then the wearer's head is vertical. When the accelerometer detects stable acceleration in the Y and Z axes with or without a stable acceleration in the X axis, then the wearer's head is tilted forward.

FIGS. 18A and 18B illustrate an optional transceiver 1810 that receives and/or transmits communication through antenna 1812. This communication may come from an adjacent contact lens, spectacle lenses, or other devices. The transceiver 1810 may be configured for two way communication with the system controller 1806. Transceiver 1810 may contain filtering, amplification, detection, and processing circuitry as is common in transceivers. The specific details of the transceiver 1810 are tailored for an electronic or powered contact lens, for example, the communication may be at the appropriate frequency, amplitude, and format for reliable communication between eyes, low power consumption, and to meet regulatory requirements. Transceiver 1810 and antenna 1812 may work in the radio frequency (RF) bands, for example, 2.4 GHz, or may use light for communication. Information received from transceiver 1810 is input to the system controller 1806, for example, information from an adjacent lens which indicates orientation. The system controller 1806 may also transmit data from, for example, the data manager 1808, to the transceiver 1810, which then transmits data over the communication link via antenna 1812. In an alternative embodiment, the transceiver 1810 and the antenna 1812 are replaced by an eyelid position sensor system to provide communication via light waves and/or blinks as discussed above.

The system controller 1806 may be implemented as a state machine, on a field-programmable gate array, in a microcontroller, or in any other suitable device. Power for the system 1800 and components described herein is supplied by a power source 1814, which may include a battery, energy harvester, or similar device as is known to one of ordinary skill in the art. The power source 1814 may also be utilized to supply power to other devices on the contact lens 1801.

The pupil position detection system 1800 in at least one embodiment is incorporated and/or otherwise encapsulated and insulated from the saline contact lens 1801 environment.

In at least one embodiment, the electronics and electronic interconnections are made in the peripheral zone of a contact lens rather than in the optic zone. In accordance with an alternative embodiment, it is important to note that the positioning of the electronics need not be limited to the peripheral zone of the contact lens. All of the electronic components described herein may be fabricated utilizing thin-film technology and/or transparent materials. If these technologies are utilized, the electronic components may be placed in any suitable location as long as they are compatible with the optics.

Figure 19:
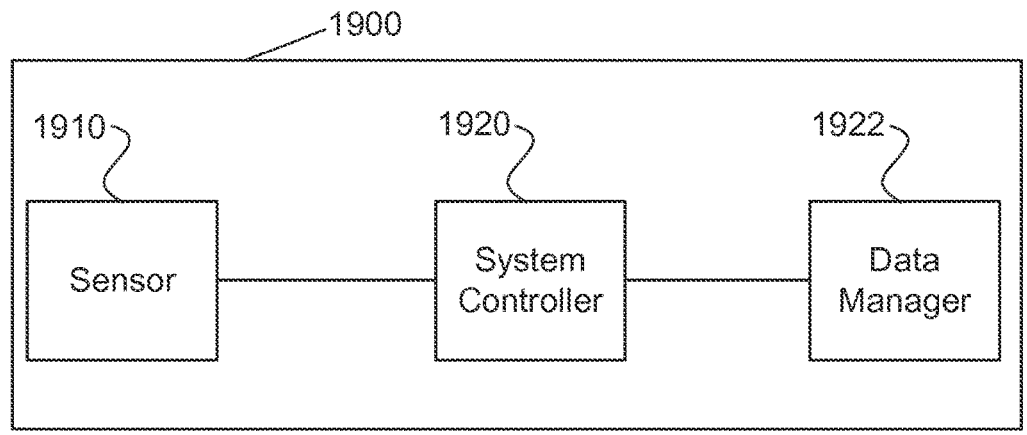
FIG. 19 illustrates a block diagram of an insertion sensor embodiment in accordance with at least one embodiment of the present invention.

In at least one embodiment as illustrated in FIG. 19, the contact lens 1900 includes a sensor 1910 to detect at least one of removal from a lens storage case and insertion of the contact lens into the wearer's eye. In at least one embodiment, insertion of the contact lens into the wearer's eye will activate sleep monitoring by the system controller 1920. In a further embodiment, the insertion will initiate an accumulator in the data manager 1922 to run. Examples of sensors that would provide detection include, but are not limited to, a pressure sensor, a reed switch, a salinity sensor, a biosensor and a capacitive sensor. These sensors, in at least one embodiment, work in conjunction with a light sensor to detect the presence of light that occurs after removal of the contact lens from the storage container. In a further embodiment to the sensor embodiments, the sampling rate used to monitor the sensor may be slowed after the detection of the event being monitored to conserve power while allowing for the detection of removal of the contact lens from the eye. In an alternative embodiment to the prior embodiment, the sensor would be deactivated upon detection of the contact lens being placed on the eye.

The pressure sensor may take a variety of forms. One example is a rear-facing (or iris-facing) pressure sensor connected to the system controller through an analog-to-digital convertor. The rear-facing pressure sensor in at least one embodiment is partially encapsulated in the contact lens while the analog-to-digital convertor is completely encapsulated in the contact lens and included as part of any circuit board present in the contact lens. The system controller resets the accumulator upon receiving a signal from the pressure sensor in excess of an insertion threshold indicating that data collection should begin by the system controller. The system controller sends a signal to the data manager to store the current accumulator value when the signal from the pressure sensor then falls below the insertion threshold indicating that the contact lens has been removed and further data collection is unnecessary. The system controller samples the pressure sensor at a predetermined schedule only when the system controller detects the eyelid is open. Another example of a pressure sensor is a pressure sensor that will detect the removal of pressure from the saline present in the storage container and would provide a signal to activate the other functionality of the contact lens. A further example of a pressure sensor is a surface acoustic wave resonator with interdigital transducer (IDT). A still further example is a binary contact pressure sensor that either detects pressure or no pressure, but not the level of pressure.

One example of a reed switch completes a circuit in the contact lens that provides power to the rest of the circuit elements by application of pressure from the wearer's eye upon insertion of the contact lens or the removal of pressure when the contact lens is removed from the storage container for use. Upon the respective event occurring, the reed switch would close and complete the circuit to provide an electrical connection between the system controller and the power supply. Another example of a reed switch use in the system is to provide a binary output upon the switch being activated with the binary output providing an indication of the switch being closed (or open depending on the orientation of the switch) as opposed to completing a circuit.

A salinity sensor or biosensor in at least one embodiment would detect salinity or another chemical present in tear fluid. Examples of the substances that could be monitored include, but are not limited to, a pathogen, a biomarker, an active agent, and a chemical. One example of a biosensor is a resistance tab, in electrical communication with system controller, that is capable of binding with the substance being monitored resulting in an increasing resistance as the amount of substance present increases. Another example is a reactive tube(s) that contains a substance, material, or mixture that may react with a specific molecule where a reaction will be indicative of the presence of a chemical being monitored. Yet another example is a biosensor in which a surface is functionalized to have affinity for a certain substance, and an electrical property of the sensor, for example capacitance or voltage, varies in response to the presence of the substance to which the sensor is functionalized. In at least one embodiment, where a chemical being monitored relates to a concentration of some substance in the tear fluid, the reaction may occur directly with that substance or may occur with a separate substance that may indicate concentration of the monitored substance. In other examples, because other electroactive biological components may affect the conductivity within a particular tube, the tube may be lined with or include a selective barrier to minimize interference with the other substances than the substance being monitored. Alternatively to a tube having an increasing conductivity in response to the presence of the monitored substance, the tube may instead have an increasing resistivity in the presence of the monitored substance. A further example will have the hollow tube include material that is selectively permeable or attractive to a specific substance or chemical. Under any of these examples, it may be possible to provide a graduated indication of the level of the substance beyond a binary output.

The capacitive sensor may be rear facing or forward facing. In at least one embodiment, the sensor would be a rear-facing sensor to allow for contact by the wearer's eye. In a further embodiment, once a contact causes a change in capacitance above an insertion threshold indicating that the contact lens has been inserted, the sensor is deactivated or has its sampling rate decreased. If, however, the sensor was forward facing, then contact by one of the eyelids that would change the capacitance above the insertion threshold would confirm insertion of the contact lens. In a further embodiment, the forward-facing capacitive sensor would also be used for detection of the position of the eyelids.

In complex systems which may include multiple sensors, such as powered ophthalmic lenses having a number of electronic components, it is preferable to reduce the potential for initiating false actions or false positive triggering of a sleep determination. In accordance with another alternative embodiment, this embodiment is directed to a decision making process and/or voting scheme which utilizes input from multiple sensors to substantially reduce the possibility of changing the state of the powered ophthalmic lens based upon inaccurate, incomplete or erroneous information, changing physiologic conditions, as well as noise and/or interference from internal and external sources. For example, in sleep detection, the control system should not determine sleep onset based upon a random blinking pattern due to eye irritation or the like. However, with input from a single sensor or erroneous information from the single sensor or other sensors, incorrect decisions may be made by the system controller. For example, without knowing the pressure applied to the ophthalmic lens, simply closing the eye lids might trigger a sleep determination despite the wearer rubbing their eyes and applying a pressure greater than lid pressure on a pressure sensor(s). In a powered ophthalmic lens having an eyelid position sensor, eyelid movement may also be utilized as a trigger for making a sleep determination. For example, when an individual gazes down to focus on a near distance object, the eyelids tend to droop and thus it may be utilized to change the state of the ophthalmic lens. Once again, if only a single input is utilized, a false action may take place due to the fact that the person is sleepy and their eyelids drooped. All of these sensors may be utilized as triggers for action to be implemented by various systems incorporated into an electronic or powered ophthalmic lens, and all of them independently or in limited combination are potentially subject to error. In addition to the sensors already mentioned which are intended to detect certain aspects directly related to determining sleep onset, other sensors may be used to improve state-change sensors by monitoring ambient conditions, noise, and interference. For example, ambient light may be monitored to improve the accuracy of blink detection, lid position, and pupil diameter sensors. Such sensors may be utilized to augment other sensors, for example, by subtracting common mode noise and interference. Sensor inputs may be used to record history readings which are then considered by a complex decision algorithm, for example, one which considers both accelerometer inputs and eye muscle contraction to determine pupil position. Utilizing the voting scheme in accordance with at least one embodiment may reduce the likelihood of error in determining whether the wearer has fallen asleep and may also allow more precise measurements. In other words, for any given determination to be made, there are sensors that may be utilized to check corroborating evidence or to augment input for a given determination by a primary sensor. It is also important to note that the sensed data, in addition to or in alternate use, may simply be utilized as part of a collection process rather than as a triggering event. For example, the sensed data may be collected, logged and utilized in treating medical conditions. In other words, it should also be appreciated that a device utilizing such a sensor may not change state in a manner visible to the user; rather the device may simply log data.

Figure 20:
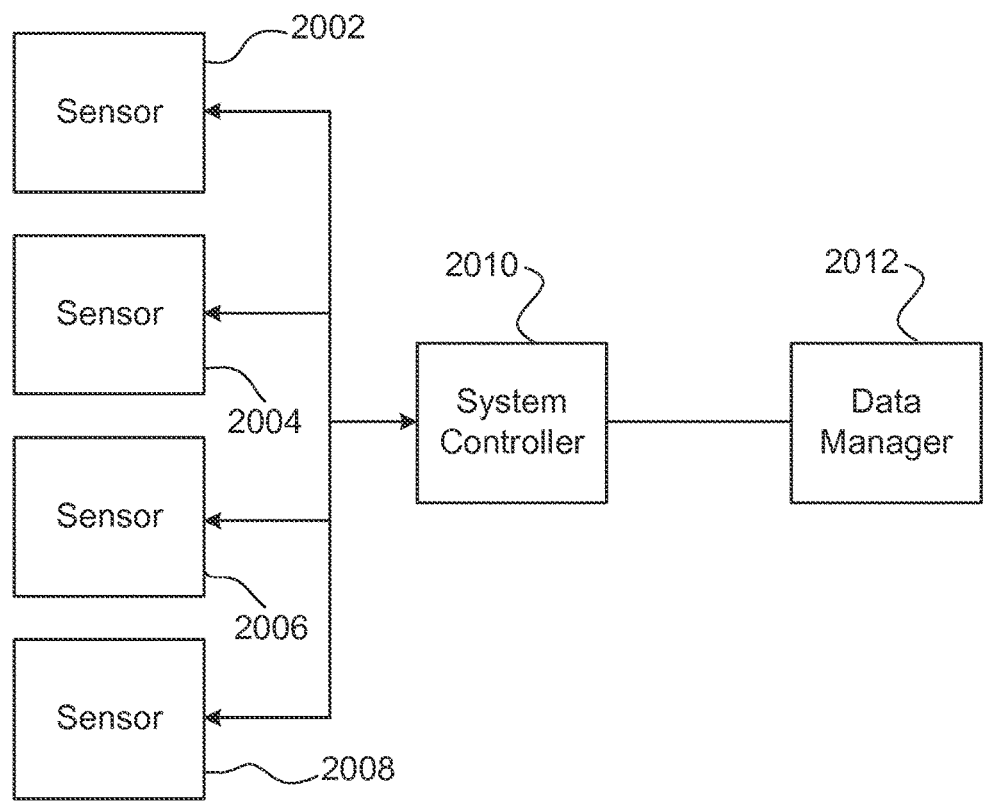
FIG. 20 illustrates a block diagram of a generic system having multiple sensors, a system controller and an alert mechanism, wherein an activation decision is made based on the output of two or more sensors in accordance with the present invention.

Referring now to FIG. 20, there is illustrated a generic system in which sensors 2002, 2004, 2006 and 2008 are used to determine if sleep onset and/or an event during sleep. The sensors 2002, 2004, 2006 and 2008 may include any number of potential inputs including blink action, lid position, pupil position, contact lens orientation, external lens pressure, and the like. The number and type of sensors is determined by the application and user. Each sensor 2002, 2004, 2006 and 2008 may have its own signal conditioning contained within the sensor block, a dedicated block, or within the system controller 2010. The system controller 2010 accepts inputs from each sensor 2002, 2004, 2006 and 2008. It then performs routines to process and compare the input data. Based on these inputs, the system controller 2010 determines if the data manager 2012 should record any readings. For example, the combination of eyelid droop, low ambient light, and vertical lens orientation may trigger the system controller 2010 to determine the wearer is drowsy and to signal the data manager 2012 to increase the sampling rate of at least one sensor system being used to make the sleep determination. Likewise, the combination of eyelid closure, vertical orientation for the wearer, and external eyelid pressure may trigger the system controller 2010 to determine no sleep onset and continue regular operation. The combination of lid closure, horizontal orientation for the wearer may trigger the system controller 2010 to determine sleep onset and to signal the alert mechanism to record data as the sleep is likely intentional sleep given the wearer's orientation. Inputs from various sensors may also be utilized to alter the configuration of the system controller to improve decision making performance, for example, if ambient light decreases, the controller may increase the gain of a photosensor. The system controller may also turn sensors on and/or off, increase and/or decrease sampling rates, and make other changes to the system to optimize performance.

Figure 21:
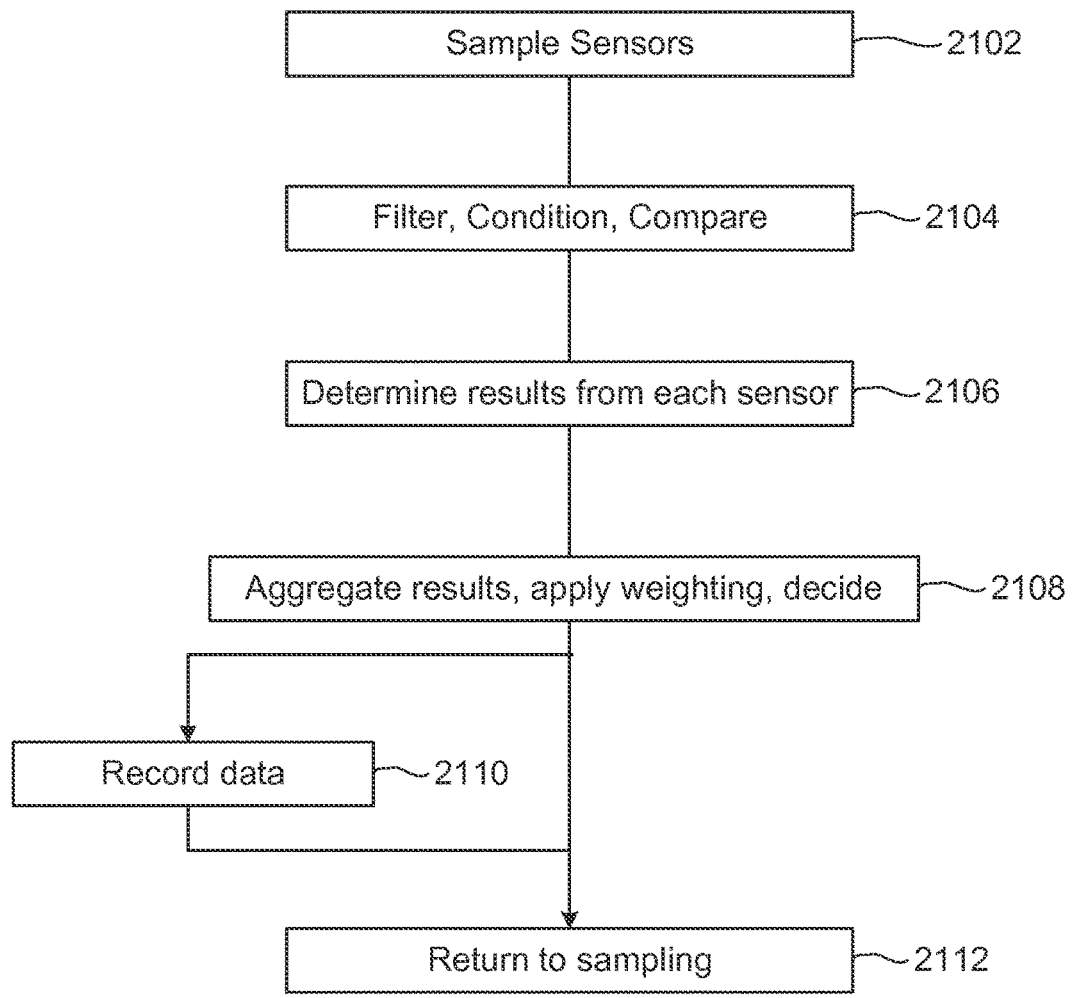
FIG. 21 illustrates a flow chart of a method by which a system controller determines if the state of an alert mechanism is to be changed based upon sensor inputs in accordance with at least one embodiment of the present invention.

FIG. 21 illustrates a method by which a system controller, for example, system controller 2010 illustrated in FIG. 20, operates to sample sensors and determine sleep status. The first step is to sample the sensors, 2102. This may require triggering other elements to activate, warm-up, calibrate, take readings, condition, and output data. The system controller may also provide configuration information to each sensor based on programmed values and current data, for example, the gain of a photosensor amplifier based on the history of incident light, or these settings may be determined by other elements in the system. Then the method performs filtering and additional conditioning, 2104, for example, digital as opposed to analog filtering, along with a comparison to baseline or reference results. One purpose of this step is to properly condition the input data for the next step so that an accurate, repeatable decision may be made. Then the results are determined from each sensor, 2106, for example, the lid position and emitter-detector response. This determination may involve comparison to a pre-programmed or variable threshold, comparison to a specific pattern, or any other determination. The results are aggregated from the previous step, weighting the results and making a decision, 2108. This step in at least one embodiment may involve per-user training and preferences, ensuring all sensors have been sampled before deciding, and various weights applied to the results of each sensor. In at least one embodiment, a decision is made that is predictable and repeatable in the presence of real-world noise and interference. If a decision is made regarding sleep status as described above, then recording data, 2110. Regardless of the decision regarding sleep status, returning the system to sampling so another set of measurements and determination may take place, 2112. The total time required to execute the process in FIG. 21 in at least one embodiment is short enough such that the system is responsive to user inputs similar to how individuals naturally interact with their environments. For example, if utilized to activate a variable-power focus lens, the system should change focus state within approximately one (1) second, similar to that of the natural accommodation system.

It should be appreciated that each sensor input may vary for reasons other than sleep. For example, the eye impedance may vary over time due to changes in body hydration, salt intake, level of exertion, or other means. Likewise, pupil diameter may vary due to changes in ambient light levels. Thus, it should be apparent that combining multiple sensor inputs reduces the chances of false positive triggering by requiring more than one input to correlate with a desired change in focal length or by using certain sensor inputs to augment other sensors.

It should also be apparent that the thresholds for each sensor and the combination of sensors used to determine sleep and/or selection of data to log during sleep depends on many variables such as safety, response time, and user preferences. The specific programming of the voting scheme may be based on clinical observations of a number of subjects and individual programming tailored to a specific user. Parameters in the voting scheme may be dependent on sensor inputs, for example, the threshold and gain setting for blink detection may vary with ambient light.

In an alternative embodiment, the system further includes a memory preservation controller that is in electrical communication with the power source and the system controller. In at least one embodiment, the memory preservation controller is an example of the resource management system 140 discussed in connection with FIG. 1A. The memory preservation controller, at a predetermined frequency, tests the power source to determine the level of energy that remains. When the remaining energy falls below a predetermined energy threshold, the memory preservation controller sends an instruction to the system controller to no longer sample the sensor system and to send a signal causing the recording by the data manager of the current time and/or accumulator value. The power then is provided to maintain the data in memory and/or data storage present on the contact lens. In a further embodiment when the power supply finds the available energy level below a low-energy threshold, the system will perform at least one of the following: reducing the sampling rate for at least one of the accelerometer and the transducer, reducing the sampling rate of at least one sensor, terminating further sampling of at least one of the accelerometer and the transducer, terminating further monitoring of the power supply, storing a time stamp representing low-energy based on the current value in the accumulator, removing power from at least one of the accelerometer and the transducer, sampling the lid closure at a second lid sampling rate that is slower than the first sampling rate, powering a memory where the readings are stored, or any combination of these. Based on this disclosure one of ordinary skill in the art should appreciate that a particular implementation may have just one of these options available and that this is contemplated to be covered by the at least one of language.

The predetermined energy threshold is based on an estimate of the power required to maintain a power supply to any memory or data storage. In a further embodiment, the threshold is adjusted based on the current run time of the lens while still facilitating an estimated period of power for the memory and/or data storage. One example of how to adjust the threshold over time is to decrement a register for each passing of a predetermined time as measured by sampling periods in the contact lens.

In a further embodiment, the energy level test is done in conjunction with the sampling of the sensor system(s) to compare the energy level of the power source to the threshold under maximum load of the lens as occurs when a sensor system(s) is providing a reading(s). If the energy level for the power source is below a threshold, then there is a high likelihood that an upcoming sensor sampling, prior to the next energy level test, will drain the power source such that the sensor system(s) will provide an incorrect reading because of insufficient power being available and/or stored data will become corrupted thus leading to a data set that is unreliable.

In a modified alternative embodiment, the memory preservation controller places an artificial load on the power source during periods of non-sampling of the sensor(s). Example sampling time periods include but are not limited to 1 minute, 2 minutes, 5 minutes, 10 minutes, 15 minutes, 20 minutes, and 30 minutes. Other examples of testing the power source include, but are not limited to, obtaining a loaded voltage, introducing a special test waveform to pulse current out the battery and measuring voltage drop with the comparison of the results being compared to a predetermined threshold that in a further embodiment can be adjusted downward in view of expected remaining run time.

In a further alternative embodiment, the memory preservation controller monitors the data manager to determine remaining space. When the remaining space in memory of the data manager is less than a free space threshold, the memory preservation controller sends a signal to the system controller to do at least one of the following: terminate sampling the sensor system(s) to avoid creating additional data for storage, send a signal to the data storage to set a flag of memory full and to shift the currently stored data to provide additional space using a first in first out approach, and remove power from the system controller and the sensor system(s) leaving power being supplied to just the data storage. Other examples include storing a time stamp representing low memory based on the current value in the accumulator, reducing the sampling rate for at least one of the accelerometer and the transducer, terminating further sampling of at least one of the accelerometer and the transducer, storing future readings from at least one of the accelerometer and the transducer over the earliest stored readings in the memory, deleting the stored sensor readings associated with the lowest accumulator reading and shifting the remaining stored sensor and accumulator readings in the memory, and any combination of these examples.

In a further embodiment to the above embodiments, the memory preservation controller and/or the resource management system is part of the system controller.

In at least one embodiment, the system further includes a storage box. The storage box in at least one embodiment includes a housing with a base and a cover that are connected along one edge to facilitate opening the cover relative to the base to allow for deposit of the contact lens into a cavity in the housing. In alternative embodiments, the storage box may include disinfecting, monitoring, reordering and external connectivity functionality. The disinfecting functionality would allow for the lenses to be used over an extended period of time by the wearer.

Figure 22:
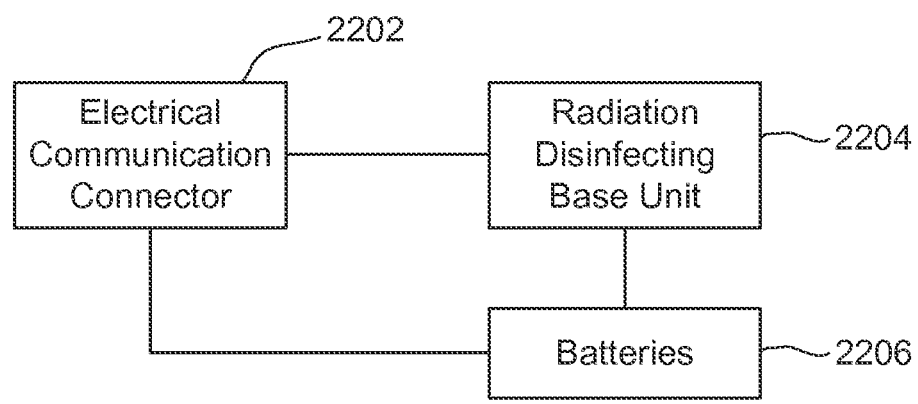
FIG. 22 illustrates a block diagram of a storage box in accordance with at least one embodiment of the present invention.

FIG. 22 illustrates an example storage box having a housing 2200, a communication system, a memory, a clock, an electrical communication connector 2202, and a power source 2206. In an alternative embodiment, the storage box includes a radiation disinfecting base unit 2204 contained within a housing such as the previously described housing and cover. The electrical communication connector 2202 may include a universal serial bus (USB) connector or other type of connector. The connector may include a terminal for transferring one or both of data and electrical power. In some embodiments, the electrical communication connector 2202 provides power to operate the radiation disinfecting base unit 2204. Some embodiments may also include one or more batteries 2206 or other power storage device. In some embodiments, the batteries 2206 include one or more lithium-ion batteries or other rechargeable device. The power storage devices may receive a charging electrical current via the electrical communication connector 2202. In at least one battery embodiment, the radiation disinfecting base unit 2204 is operational via stored power in the batteries 2206.

In at least one embodiment, the communication system includes an antenna such as a radio-frequency identification (RFID) antenna for interacting with inserted lenses and a controller electrically communicating with said antenna. In at least one embodiment, the controller is in electrical communication with at least one memory, which in at least one embodiment is flash memory like that used in a memory stick. Examples of the interaction include wireless recharging of the power source on one or both lenses, transferring data stored on the lens(es) to memory in (or in communication with) the storage box, and transferring templates and masks based on wearer-specific characteristics from the storage box to at least one lens. In an alternative embodiment, the antenna is used to communicate with an external device such as a computer or smart phone.

In at least one embodiment, the controller is configured to translate and/or format the data received from the at least one lens to change the time stamp information into actual times based on the current accumulator reading at the time of data transfer as correlated to the current time on the storage box. In an alternative embodiment, the storage box sends a signal to the lens to reset the accumulator to zero and the processor records in memory the time that the accumulator was reset to zero. After reinsertion of the lens into the storage box, the processor notes the current time and determines the number of sampling cycles. In the embodiments where the sampling cycles are of different lengths depending on what is being sampled and/or operational state of the lens(es) since removal of the lens(es), the storage box normalizes the sample periods over the time difference between removal of the lens(es) from the storage box and return of the lens(es) to the storage box as measured by the storage box.

In some embodiments, the electrical communication connector 2102 may include a simple source of AC or DC current. In such embodiments, the power source 2106 may be omitted as power is provided through the electrical communication connector 2102.

An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses.

Figure 23:
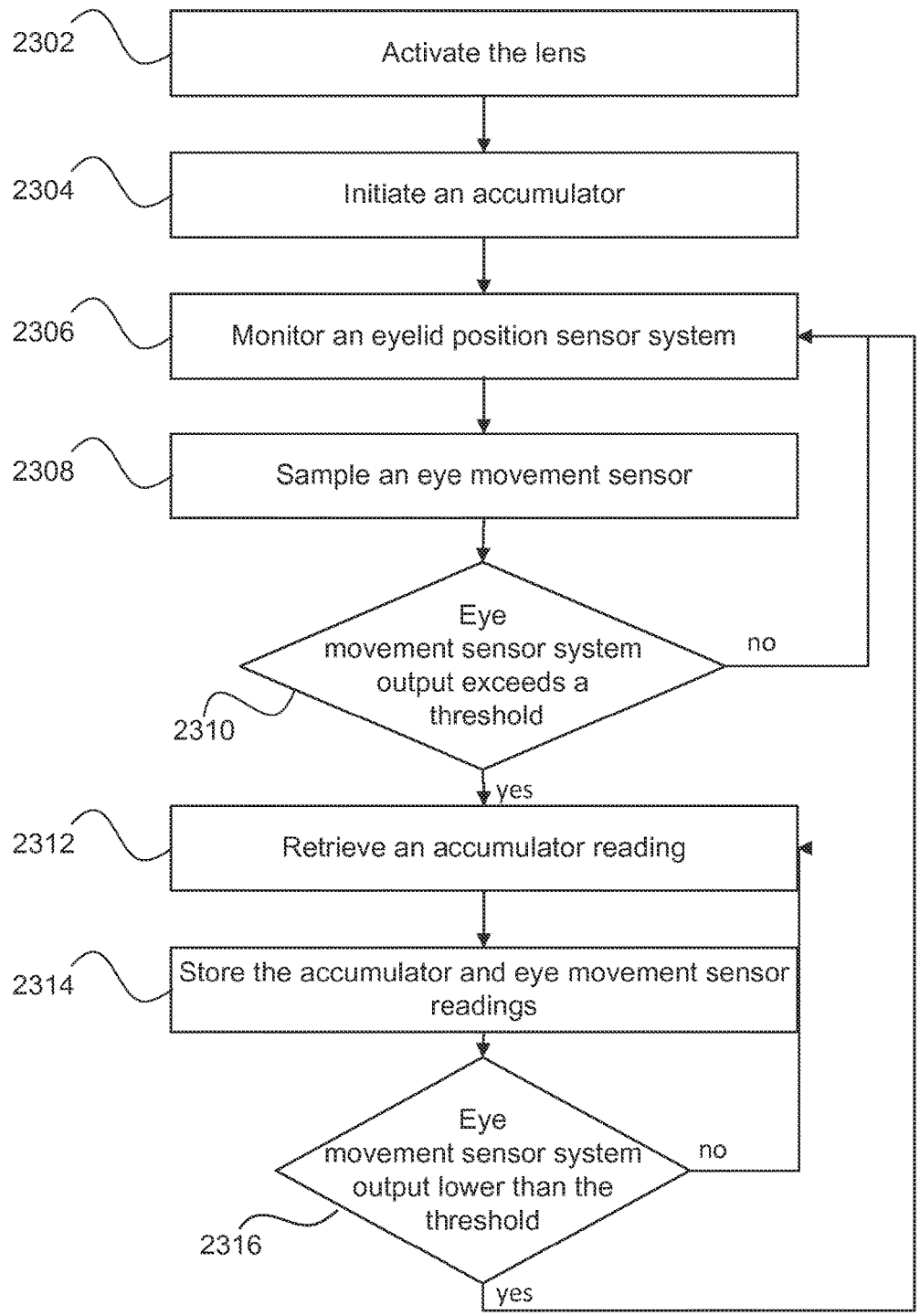
FIG. 23 illustrates a flow chart of a method by which a system controller monitors sleep in accordance with at least one embodiment of the present invention.

FIG. 23 illustrates a method for monitoring sleep with a powered ophthalmic lens. As discussed above, there are a variety of ways to activate the powered ophthalmic lens, 2302. In at least one embodiment, in response to activation of the powered ophthalmic lens or alternatively a sleep monitoring operation state, an accumulator is initiated on the lens to track a passage of time, 2304. The system controller monitors the eyelid position sensor system for whether the eyelid(s) has closed at a first sampling rate, 2306. When the system controller detects the eyelid has closed, an eye movement sensor system (such as an accelerometer and/or a transducer) is sampled, 2308. The system controller determines whether the reading from the eye movement sensor system exceeds a threshold, 2310. In at least one embodiment, when the threshold is exceeded, then this is indicative of REM sleep. When the threshold is exceeded, the system controller retrieves a reading from the accumulator, 2312, and stores the accumulator reading with the eye movement sensor reading, 2314. The system controller monitors the eye movement sensor to determine when the reading is below the threshold to indicate in at least one embodiment the end of REM sleep prior to returning to sampling eyelid closure readings, 2316.

In an alternative embodiment, the sampling of and storing of data from the eyelid position sensor system and the eye movement sensor system occurs with or without an accumulator begins once the ophthalmic lens is activated for data collection. The data is transferred to an external device (e.g., external device 1390 in FIG. 13B) for analysis and/or review during the data collection or after data collection has begun. In a further embodiment, the sampling and storing continue until a terminate signal is received indicating the end of the data collection and/or a resource management system determines there are insufficient resources available. In a further alternative embodiment, instead of storing the data, the data is transmitted to the external device In a further embodiment, a level of light is measured with a photosensor present on the contact lens. The light level reading is stored as an initial light level along with a reading from the accumulator by, for example, the data manager. The system controller monitors the photosensor to determine when a change in light level occurs and storing the current reading from the accumulator with the light level reading. This allows for the level of ambient light to be monitored while the eyelids are open to allow for analysis of the sleep pattern. In a further embodiment, the system controller compares the accumulator reading to a duration threshold. When the accumulator exceeds the duration threshold, the system controller samples the photosensor to determine if the current light level approximates the initial light level reading such that when the initial light level is reached the sleep monitoring is terminated. In at least one embodiment this allows for reduced sampling and monitoring of the current light level until an anticipated sleep time has passed.

In at least one embodiment, the sampling rates of the eyelid position sensor and/or the eye position sensor is changed to a second sampling rate (e.g., a second lid sampling rate and a second motion sampling rate). In at least one embodiment, the second sampling rates are slower while in another embodiment the second sampling rates are faster.

In at least one embodiment, the contact lens performs the method in conjunction with an external device that in at least one embodiment provides storage and/or processing power. The contact lens when storing a reading also transmits the reading to the external device for storage. In an alternative embodiment, the contact lens does not store the reading and relies on the external device to store the reading. In at least one embodiment, the external device stores the reading along with a time stamp based on the current time on the external device, while in an alternative embodiment the external device adjusts the time stamp to take into account transmission time between the contact lens and the external device. In at least one embodiment, the external device samples light levels with, for example, a camera or other CCD, to store the light level with a time stamp in memory on the external device. In at least one embodiment as discussed previously, the external device may provide an interface that allows for user input regarding initiation of a sleep study and a termination of a sleep study.

Figure 24:
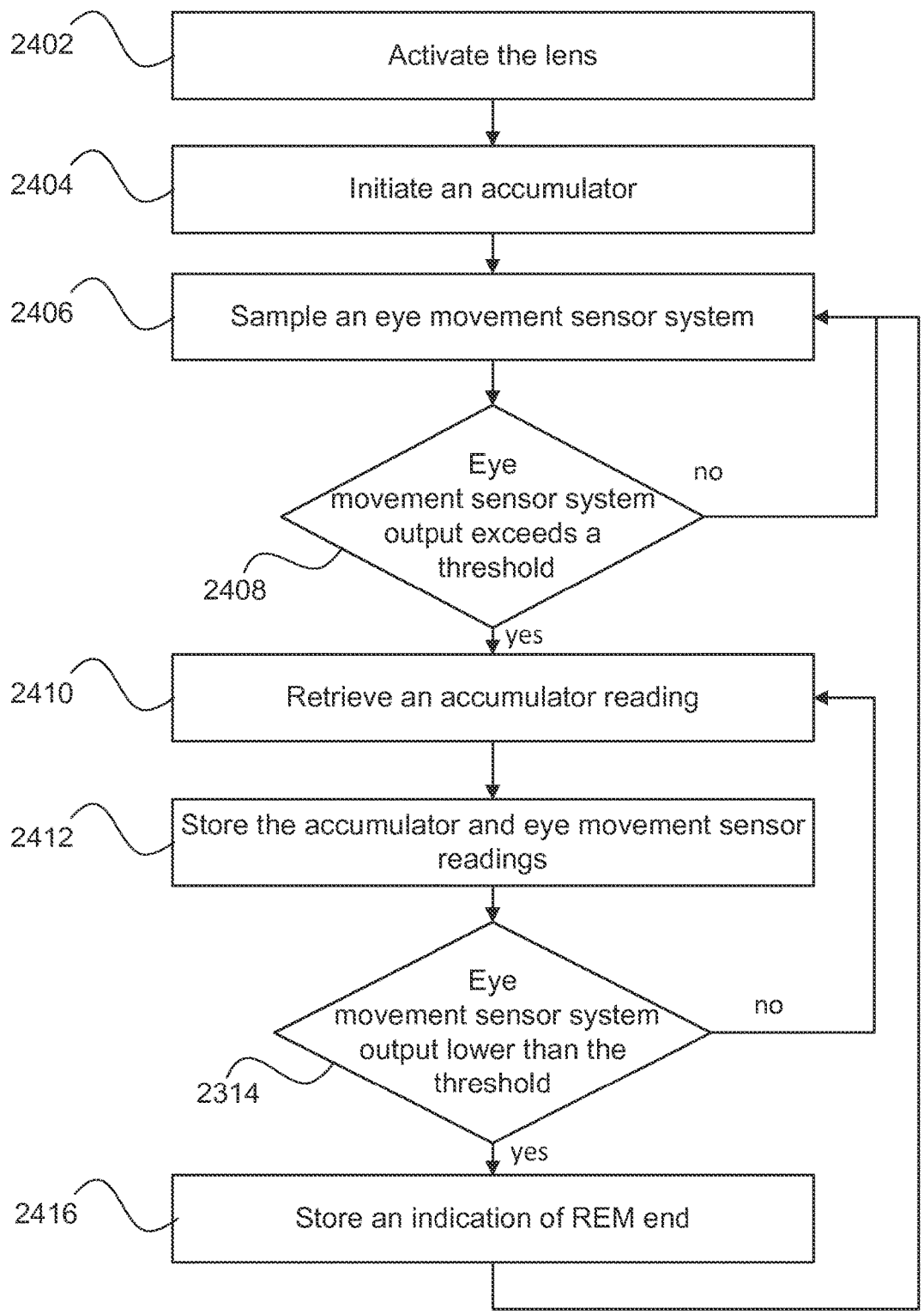
FIG. 24 illustrates a flow chart of a method by which a system controller monitors sleep in accordance with at least one embodiment of the present invention.

In an alternative method embodiment illustrated in FIG. 24, the powered ophthalmic lens is activated, 2402, although in at least one embodiment this step is omitted. The system controller and/or the data manager initiates an accumulator to track a passage of time, 2404. The system controller samples an eye position sensor such as an accelerometer or a transducer, 2406, where in at least one embodiment this sampling occurs at least once. The reading received from the eye position sensor is compared to a threshold by the system controller, 2408, such that when the threshold is exceeded the system controller and/or data manager: retrieves a reading from the accumulator, 2410; stores the accumulator reading and the eye position sensor reading, 2412; and determines whether a later sampled reading is below the threshold, 2414, such that when the reading is below the threshold storing an indication of a REM end, 2416. In at least one embodiment, the thresholds are different values while in another embodiment the thresholds are the same threshold with the thresholds being a first threshold and a second threshold. In a variety of alternative embodiments, the embodiments discussed in addition to the method illustrated in FIG. 23 work in conjunction with the method illustrated in FIG. 24.

Figure 25:
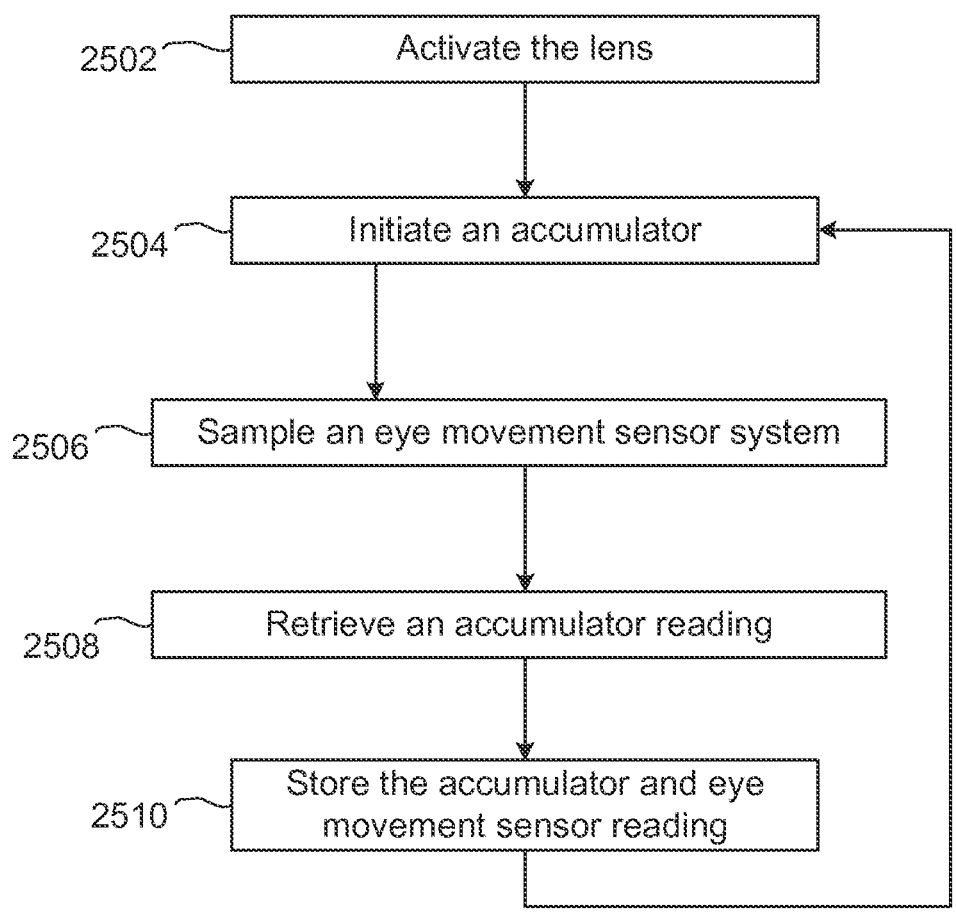
FIG. 25 illustrates a flow chart of a method by which a system controller monitors sleep in accordance with at least one embodiment of the present invention.

In an alternative method embodiment illustrated in FIG. 25, the lens is activated, 2502, although in at least one embodiment this step is omitted. The system controller and/or the data manager initiates an accumulator to track a passage of time, 2504. The system controller samples an eye position sensor such as an accelerometer or a transducer, 2506, where in at least one embodiment this sampling occurs at least once. The system controller and/or data manager: retrieves a reading from the accumulator, 2508; then stores the accumulator reading and the eye position sensor reading, 2510. In at least one embodiment, the sampling, retrieving and storing steps are repeated until deactivation or termination of the method occurs with examples including the various approaches discussed previously.

Although shown and described in what is believed to be the most practical embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for monitoring sleep with a powered contact lens, the method comprising:
   disposing with the contact lens a processor, a clock, an eye movement sensor, and a computer readable storage medium having instructions stored therein, which when executed by the processor, cause the powered contact lens to perform the steps of:
   activating the powered contact lens;
   initiating the clock within the lens to track a passage of time;
   determining at a first eyelid sampling rate whether eyelid closure has occurred;
   when eyelid closure is detected,
      sampling at least once the eye movement sensor within the contact lens, and
      determining whether an eye movement threshold is exceeded, when the eye movement threshold is exceeded,
         retrieving a time stamp from the clock;
         storing the time stamp and a reading of the eye movement sensor; and
         determining whether the reading is below the eye movement threshold, when the reading is below the eye movement threshold, storing an indication of an ending of a rapid eye movement (REM) and returning to determining whether eyelid closure has occurred.

2. The method according to claim 1, further comprising:
   measuring a light level with at least one photosensor present on the lens;
   storing the light level and current reading from the clock; and
   determining when a change in light level occurs and storing the current time stamp from the clock with the light level reading.

3. The method according to claim 2, further comprising:
   comparing the clock to a duration threshold associated with an anticipated sleep time; and
   when the clock is in excess of the duration threshold, determining if the current light level approximates the initial light level reading, when initial light level is reached, terminating sleep monitoring.

4. The method according to claim 1, wherein sampling of the eye movement sensor occurs at a first motion sampling rate until the reading exceeds the threshold, then sampling at a second motion sampling rate.

5. The method according to claim 1, wherein when eyelid closure is detected, then sampling eyelid closure at a second eyelid sampling rate that is slower than the first sampling rate.

6. The method according to claim 1, further comprising:
   monitoring a power supply on the lens for an available energy level;

when the power supply has the available energy level below a low energy threshold, performing at least one of reducing the sampling rate for the eye movement sensor, reducing the sampling rate of an eyelid position sensor, terminating further sampling of the eye position sensor, terminating further monitoring of the power supply, storing a time stamp representing low energy based on the current value of the clock, removing power from the eye position sensor, sampling the eyelid position sensor at a second eyelid sampling rate that is slower than the first sampling rate, and powering a memory where the readings are stored.

7. The method according to claim 1, further comprising:

monitoring available memory for storing readings;

when the available memory is below a low memory threshold, performing at least one of storing a time stamp representing low memory based on the current value of the clock, reducing the sampling rate for the eye movement sensor, terminating further sampling of the eye movement sensor, storing future of readings the eye movement sensor over the earliest stored readings in the memory, and deleting the stored sensor readings associated with the lowest clock reading and shifting the remaining stored sensor and clock readings in the memory.

8. The method according to claim 1, wherein storing the readings includes transmitting the readings to an external device for storage.

9. The method according to claim 8, wherein the external device stores the readings with a time stamp based on the current time on the external device.

10. The method according to claim 8, further comprising:

sampling light levels with the external device and storing the light level with a time stamp in memory.

11. The method according to claim 8, further comprising receiving with the external device user input for initiation of a sleep study and a termination of the sleep study.

12. A method for monitoring sleep with a powered contact lens, the method comprising:

disposing with the contact lens a processor, a clock, an eye movement sensor, and a computer readable storage medium having instructions stored therein, which when executed by the processor, cause the powered contact lens to perform the steps of:

activating the powered contact lens;

initiating the clock within the lens to track a passage of time;

sampling at least once the eye movement sensor within the contact lens; and determining whether a first eye movement threshold is exceeded, when the first eye movement threshold is exceeded retrieving a time stamp from the clock, storing the time stamp accumulator reading and a reading of the eye movement sensor at least one of the accelerometer, and determining whether the reading is below a second eye movement threshold, when the reading is below the second eye movement threshold, storing of an ending of a rapid eye movement (REM).

13. The method according to claim 12, wherein sampling of the eye movement sensor occurs at a first eye movement sampling rate until the reading exceeds the eye movement threshold, then sampling at a second eye movement sampling rate.

14. The method according to claim 12, further comprising:

monitoring a power supply on the lens for an available energy level;

when the power supply has the available energy level below a low energy threshold, performing at least one of reducing the sampling rate for the eye movement sensor, reducing the sampling rate of at least one sensor, terminating further sampling of the eye movement sensor, terminating further monitoring of the power supply, storing a time stamp representing low energy based on the current value of the clock, removing power from the eye movement sensor, and powering a memory where the readings are stored.

15. The method according to claim 12, further comprising:

monitoring available memory for storing readings;

when the available memory is below a low memory threshold, performing at least one of storing a time stamp representing low memory based on the current value of the clock, reducing the sampling rate the eye movement sensor, terminating further sampling of the eye movement sensor, storing future readings from the eye movement sensor over the earliest stored readings in the memory, and deleting the stored sensor readings associated with the lowest clock reading and shifting the remaining stored sensor and clock readings in the memory.

16. The method according to claim 12, wherein any storing reading includes transmitting the reading to an external device for storage.

* * * * *